(12) United States Patent
Goldberg et al.

(10) Patent No.: US 12,734,363 B2
(45) Date of Patent: Sep. 15, 2026

(54) ASSEMBLIES, APPARATUSES, AND METHODS FOR ELECTRICALLY STIMULATING THE BODY

(71) Applicant: EDWARDS LIFESCIENCES CORPORATION, Irvine, CA (US)

(72) Inventors: Eran Goldberg, Nesher (IL); Oren Cohen, Kadima (IL)

(73) Assignee: Edwards Lifesciences Corporation, Irvine, CA (US)

( * ) Notice: Subject to any disclaimer, the term of this patent is extended or adjusted under 35 U.S.C. 154(b) by 467 days.

(21) Appl. No.: 18/141,889

(22) Filed: May 1, 2023

(65) Prior Publication Data

US 2023/0264028 A1 Aug. 24, 2023

Related U.S. Application Data

(63) Continuation of application No. PCT/US2021/057711, filed on Nov. 2, 2021.

(60) Provisional application No. 63/108,537, filed on Nov. 2, 2020.

(51) Int. Cl.

*A61N 1/36* (2006.01)
*A61N 1/05* (2006.01)
*A61N 1/362* (2006.01)

(52) U.S. Cl.

CPC ........... *A61N 1/362* (2013.01); *A61N 1/0565* (2013.01)

(58) Field of Classification Search

CPC ...... A61N 1/362; A61N 1/0565; A61N 1/056; A61F 2/9517; A61F 2/2433

See application file for complete search history.

(56) References Cited

U.S. PATENT DOCUMENTS

| | | | | |
|---|---|---|---|---|
| 519,297 | A | 5/1894 | Wanek et al. | |
| 3,610,877 | A * | 10/1971 | Driscoll | B23K 35/0205 219/68 |
| 4,035,849 | A | 7/1977 | Angell et al. | |
| 4,592,340 | A | 6/1986 | Boyles | |
| 4,955,895 | A | 9/1990 | Sugiyama et al. | |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Rex R Holmes
(74) *Attorney, Agent, or Firm* — Klarquist Sparkman, LLP

(57) ABSTRACT

This disclosure is directed to assemblies, apparatuses, and methods for electrically stimulating the body. In one example, a medical apparatus comprises a handle comprising an electrical connection assembly that is configured to establish an electrical connection between a guidewire and an electrode of an external electrical stimulation generator and that is configured to maintain this electrical connection when the guidewire moves longitudinally relative to the handle, or vice versa. The guidewire may be configured to electrically contact tissue of a patient to deliver electrical stimulation to the tissue. In some examples, the medical apparatus may be included in a medical assembly comprising an introducer device that is configured to facilitate subcutaneous insertion of the medical apparatus. The introducer device may be configured to be electrically connected to electrical stimulation generator and may be configured to electrically contact tissue of the patient.

23 Claims, 11 Drawing Sheets

(56) References Cited

U.S. PATENT DOCUMENTS 4,994,077 A 2/1991 Dobben
5,059,177 A 10/1991 Towne et al.
5,176,698 A 1/1993 Burns et al.
5,192,297 A 3/1993 Hull
5,266,073 A 11/1993 Wall
5,325,845 A 7/1994 Adair
5,358,496 A 10/1994 Ortiz et al.
5,411,552 A 5/1995 Andersen et al.
5,554,185 A 9/1996 Block et al.
5,591,195 A 1/1997 Taheri et al.
5,599,305 A 2/1997 Hermann et al.
5,632,760 A 5/1997 Sheiban et al.
5,639,274 A 6/1997 Fischell et al.
5,728,068 A 3/1998 Leone et al.
5,749,890 A 5/1998 Shaknovich
5,782,809 A 7/1998 Umeno et al.
5,824,044 A 10/1998 Quiachon et al.
5,840,081 A 11/1998 Andersen et al.
5,908,405 A 6/1999 Imran et al.
5,916,147 A 6/1999 Boury
5,931,819 A * 8/1999 Fariabi .............. A61M 25/0158 604/525
5,944,690 A 8/1999 Falwell et al.
5,961,536 A 10/1999 Mickley et al.
5,968,068 A 10/1999 Dehdashtian et al.
6,019,777 A 2/2000 Mackenzie
6,027,510 A 2/2000 Alt
6,033,381 A 3/2000 Kontos
6,143,016 A 11/2000 Bleam et al.
6,162,208 A 12/2000 Hipps
6,168,614 B1 1/2001 Andersen et al.
6,174,327 B1 1/2001 Mertens et al.
6,217,585 B1 4/2001 Houser et al.
6,235,050 B1 5/2001 Quiachon et al.
6,251,092 B1 6/2001 Qin et al.
6,379,372 B1 4/2002 Dehdashtian et al.
6,383,171 B1 5/2002 Gifford et al.
6,454,799 B1 9/2002 Schreck
6,458,153 B1 10/2002 Bailey et al.
6,461,382 B1 10/2002 Cao
6,471,672 B1 10/2002 Brown et al.
6,500,147 B2 12/2002 Omaleki et al.
6,514,228 B1 2/2003 Hamilton et al.
6,527,979 B2 3/2003 Constantz et al.
6,579,305 B1 6/2003 Lashinski
6,582,462 B1 6/2003 Andersen et al.
6,652,578 B2 11/2003 Bailey et al.
6,730,118 B2 5/2004 Spenser et al.
6,733,525 B2 5/2004 Yang et al.
6,764,504 B2 7/2004 Wang et al.
6,767,362 B2 7/2004 Schreck
6,830,584 B1 12/2004 Seguin
6,893,460 B2 5/2005 Spenser et al.
6,908,481 B2 6/2005 Cribier
7,011,094 B2 3/2006 Rapacki et al.
7,018,406 B2 3/2006 Seguin et al.
7,018,408 B2 3/2006 Bailey et al.
7,137,993 B2 11/2006 Acosta et al.
7,276,084 B2 10/2007 Yang et al.
7,318,278 B2 1/2008 Zhang et al.
7,320,702 B2 1/2008 Hammersmark et al.
7,320,704 B2 1/2008 Lashinski et al.
7,374,571 B2 5/2008 Pease et al.
7,393,360 B2 7/2008 Spenser et al.
7,435,257 B2 10/2008 Lashinski et al.
7,510,575 B2 3/2009 Spenser et al.
7,585,321 B2 9/2009 Cribier
7,594,926 B2 9/2009 Linder et al.
7,597,709 B2 10/2009 Goodin
7,618,446 B2 11/2009 Andersen et al.
7,780,723 B2 8/2010 Taylor
7,785,366 B2 8/2010 Maurer et al.
7,959,661 B2 6/2011 Hijlkema et al.
8,029,556 B2 10/2011 Rowe
8,167,932 B2 5/2012 Bourang et al.
RE43,882 E 12/2012 Hopkins et al.
8,449,606 B2 5/2013 Eliasen et al.
8,475,523 B2 7/2013 Duffy
8,568,472 B2 10/2013 Marchand et al.
9,061,119 B2 6/2015 Le et al.
9,119,716 B2 9/2015 Lee et al.
9,795,477 B2 10/2017 Tran et al.
11,273,038 B2 3/2022 Tang et al.
2001/0002445 A1 5/2001 Vesely
2001/0007082 A1 7/2001 Dusbabek et al.
2002/0032481 A1 3/2002 Gabbay
2002/0058995 A1 5/2002 Stevens
2002/0161421 A1* 10/2002 Lee ...................... G01R 33/285 607/116
2002/0165461 A1 11/2002 Hayzelden et al.
2003/0040792 A1 2/2003 Gabbay
2003/0050694 A1 3/2003 Yang et al.
2003/0120341 A1 6/2003 Shennib et al.
2004/0093061 A1 5/2004 Acosta et al.
2004/0133263 A1 7/2004 Dusbabek et al.
2004/0143197 A1 7/2004 Soukup et al.
2004/0186563 A1 9/2004 Lobbi
2004/0186565 A1 9/2004 Schreck
2004/0260389 A1 12/2004 Case et al.
2005/0080474 A1 4/2005 Andreas et al.
2005/0096736 A1 5/2005 Osse et al.
2005/0137689 A1 6/2005 Salahieh et al.
2005/0149160 A1 7/2005 McFerran
2005/0203614 A1 9/2005 Forster et al.
2005/0203617 A1 9/2005 Forster et al.
2005/0245894 A1 11/2005 Azizi
2006/0025857 A1 2/2006 Bergheim et al.
2006/0282150 A1 12/2006 Olson et al.
2007/0005131 A1 1/2007 Taylor
2007/0073389 A1 3/2007 Bolduc et al.
2007/0088431 A1 4/2007 Bourang et al.
2007/0100356 A1 5/2007 Lucatero et al.
2007/0112422 A1 5/2007 Dehdashtian
2007/0203575 A1 8/2007 Forster et al.
2007/0219612 A1 9/2007 Andreas et al.
2007/0239254 A1 10/2007 Chia et al.
2007/0244546 A1 10/2007 Francis
2007/0265700 A1 11/2007 Eliasen et al.
2008/0065011 A1 3/2008 Marchand et al.
2008/0103520 A1 5/2008 Selkee
2008/0125853 A1 5/2008 Bailey et al.
2008/0294230 A1 11/2008 Parker
2009/0024428 A1 1/2009 Hudock
2009/0069889 A1 3/2009 Suri et al.
2009/0138079 A1 5/2009 Tuval et al.
2009/0157175 A1 6/2009 Benichou
2009/0192585 A1 7/2009 Bloom et al.
2009/0228093 A1 9/2009 Taylor et al.
2009/0276040 A1 11/2009 Rowe et al.
2009/0281619 A1 11/2009 Le et al.
2009/0299456 A1 12/2009 Melsheimer
2009/0319037 A1 12/2009 Rowe et al.
2010/0030318 A1 2/2010 Berra
2010/0036472 A1 2/2010 Papp
2010/0036473 A1 2/2010 Roth
2010/0049313 A1 2/2010 Alon et al.
2010/0076402 A1 3/2010 Mazzone et al.
2010/0076541 A1 3/2010 Kumoyama
2010/0082089 A1 4/2010 Quadri et al.
2010/0094394 A1 4/2010 Beach et al.
2010/0121425 A1 5/2010 Shimada
2010/0145431 A1 6/2010 Wu et al.
2010/0161036 A1 6/2010 Pintor et al.
2010/0174349 A1* 7/2010 Stevenson ................ A61N 1/05 607/116
2010/0174363 A1 7/2010 Castro
2010/0198347 A1 8/2010 Zakay et al.
2010/0274344 A1 10/2010 Dusbabek et al.
2011/0015729 A1 1/2011 Jimenez et al.
2011/0054596 A1 3/2011 Taylor
2011/0137331 A1 6/2011 Walsh et al.
2011/0160846 A1 6/2011 Bishop et al.
2012/0123529 A1 5/2012 Levi et al.
2012/0239142 A1 9/2012 Liu et al.

(56) References Cited

U.S. PATENT DOCUMENTS

| | | | | |
|---|---|---|---|---|
| 2013/0030519 | A1 | 1/2013 | Tran et al. | |
| 2013/0317598 | A1 | 11/2013 | Rowe et al. | |
| 2014/0296962 | A1 | 10/2014 | Cartledge et al. | |
| 2017/0065415 | A1 | 3/2017 | Rupp et al. | |
| 2017/0266434 | A1* | 9/2017 | Daniels | A61N 1/056 |
| 2018/0153689 | A1 | 6/2018 | Maimon et al. | |
| 2018/0344456 | A1 | 12/2018 | Barash et al. | |

FOREIGN PATENT DOCUMENTS

| | | | |
|---|---|---|---|
| EP | 0592410 | B1 | 10/1995 |
| EP | 0850607 | A1 | 7/1998 |
| FR | 2815844 | A1 | 5/2002 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A1 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |

* cited by examiner 124
113
103
102
134
100
104
107
105
112
108
106
110

124
110
118
122
128
130
114
112
108
126
120
118
105
104

200
202
203
204
206
208
210
211
212
216
218
220
222
224
226
228
230
232
234
236
238
239
240
242
300
302
303
304
306
308
310
311
312
316
318
320
322
324
326
328
330
332
334
336
338
340
341
344

ASSEMBLIES, APPARATUSES, AND METHODS FOR ELECTRICALLY STIMULATING THE BODY

CROSS-REFERENCE TO RELATED APPLICATIONS

The present application is a continuation of a PCT Application No. PCT/US2021/057711, filed Nov. 2, 2021, which claims the benefit of U.S. Provisional Application No. 63/108,537, filed Nov. 2, 2020, both of which applications are incorporated herein by reference.

FIELD

This disclosure relates to assemblies, apparatuses, and methods for electrically stimulating the body, and in particular to assemblies, apparatuses, and methods for electrically connecting electrodes to an electrical stimulator.

BACKGROUND

Medical personnel (e.g., physicians) may electrically stimulate one or more areas of a patient's body (e.g., heart, brain, spinal cord, and/or other organs and/or tissue) during a medical procedure. For example, medical personnel may electrically stimulate the heart to pace and/or otherwise control the beating of the heart during various heart valve repair and/or replacement procedures. For example, some heart valve repair and/or replacement procedures, such as valvuloplasty and transcatheter heart valve replacement procedures (e.g., transcatheter aortic valve implantation (TAVI) procedures), employ medical devices that require the physician to hold open the native heart valve (e.g., by rapidly pacing the heart) in order to accommodate and/or support the medical devices. For example, a physician may rapidly pace the heart to stop the flow of blood when positioning and/or radially expanding such medical devices (e.g., inflatable balloon catheters and/or expandable transcatheter prosthetic heart valves) within the native heart valve.

Typically, a physician may rapidly pace and/or otherwise electrically stimulate the heart by electrically connecting electrodes (e.g., anode and cathode) of an electrical stimulator (e.g., pacing device) to the patient's vasculature at different locations on the patient's body. As one example, during a TAVI procedure, a physician may attach the lead (e.g., alligator clip) of the pacing device's cathode to a proximal portion of a guidewire (i.e., a portion of the guidewire that is positioned outside the patient and is therefore readily accessible to the physician) after having advanced the guidewire through the patient's vasculature into electrical contact with the tissue of the left ventricle. Further, the physician may attach the lead of the pacing device's anode to a needle inserted into the patient's skin near the insertion site at the groin. Because the guidewire serves as one of the stimulating electrodes, such pacing systems do not require a separate pacing wire and thus are simpler and cheaper than other pacing systems that utilize such standalone pacing wires in conjunction with the guidewire.

However, because the leads (e.g., alligator clips) of such pacing systems are fully exposed, they may pose a safety risk to the patient and/or the medical personnel. Further, such pacing systems are difficult to use because they require considerable precision. Specifically, because the guidewire and cathode lead cannot move relative to one another once clipped together, the physician may not be able to reposition the guidewire and/or medical apparatus after attaching the cathode lead to the guidewire. As such, the physician may have to precisely position the guidewire and/or medical apparatus in their rapid pacing positions before attaching the cathode lead to the guidewire. Thus, safer and easier-to-use assemblies and apparatuses are desired for electrically stimulating and/or pacing the heart.

SUMMARY

The present disclosure relates to assemblies, apparatuses, and methods for electrically stimulating a patient's body. Specifically, this disclosure relates to assemblies, apparatuses, and methods for electrically connecting electrodes to an electrical stimulator so that the electrodes can electrically stimulate a desired location, area, and/or region within the patient's body. For example, a physician may electrically stimulate the heart to rapidly pace the heart, stop the flow of blood through a native heart valve, and/or hold open a native heart valve during transcatheter heart valve replacement procedures, valvuloplasty, and/or other heart valve repair and/or replacement procedures. In some examples, a handle of a medical apparatus (e.g., endovascular delivery device) is configured to electrically connect a guidewire to the electrical stimulator. In this way, the guidewire can serve as an electrode that provides electrical stimulation to the patient's body. In some examples, an introducer device that is typically used to facilitate subcutaneous insertion of the medical apparatus, also may be configured to electrically connect to the electrical stimulator and serve as a second electrode.

In one representative example, a medical apparatus for insertion into a patient's vasculature via catheterization comprises a handle comprising a housing and an electrical connection assembly. The housing is configured to slidably coupled to a guidewire when the guidewire is inserted through the housing, and the electrical connection assembly is configured to be electrically connected to the guidewire and to an electrode of an external electrical stimulation generator to provide an electrical connection between the external electrical stimulation generator and the guidewire. The electrical connection assembly comprises at least one electrical contacting structure configured to maintain electrical contact with the guidewire as the guidewire moves longitudinally relative to the handle, or vice versa.

In another representative example, a medical assembly for rapidly pacing a heart of a patient comprises an introducer device and a medical apparatus. The introducer device is configured to be electrically connected to a first location within a vasculature of the patient and the medical apparatus is configured to be electrically connected to a guidewire that is electrically connected to a second location within the vasculature of the patient. Further, the introducer device is configured to be electrically connected to a first electrode of an electric power source and the medical apparatus is configured to be electrically connected to a second electrode of the electric power source, wherein the first and second electrodes have opposite polarities.

In yet another representative example, a medical assembly for rapidly pacing a heart comprises an electric power source, a guidewire, an introducer device that is configured to extend over the guidewire and configured to be electrically connected to the electric power source, and a medical apparatus that is configured to extend over the guidewire and through the introducer device and that is configured to electrically connect the electric power source to the guidewire. The electric power source comprises a first electrode having a first polarity and a second electrode having a second polarity that is opposite the first polarity. The guidewire is configured to be inserted into a vasculature of a patient and through a native valve of a heart of the patient. The guidewire is configured to be electrically connected to the vasculature at a first location of the vasculature. The introducer device is configured to be electrically connected to the vasculature at a second location of the vasculature, and is configured to be electrically connected to the second electrode of the electric power source to provide an electrical connection between the second electrode of the electric power source and the second location of the vasculature. The medical apparatus is configured to be electrically connected to the first electrode of the electric power source and is further configured to be electrically connected to the guidewire to provide an electrical connection between the first electrode of the electric power source and the first location of the vasculature.

In some such examples, the medical assembly further comprises a handle comprising a housing configured to be slidably coupled to the guidewire and an electrical connection assembly that is configured to be electrically connected to the second electrode of the electric power source and to the guidewire to provide an electrical connection between the second electrode of the electric power source and the guidewire. The electrical connection assembly comprises at least one electrical contacting structure configured to maintain electrical contact with the guidewire as the guidewire moves longitudinally relative to the handle, or vice versa.

In yet another representative example, a method for rapidly pacing a heart with a medical apparatus comprises: inserting a guidewire through a surgical opening, a vasculature of a patient, and a native valve of a heart of the patient, advancing the medical apparatus over the guidewire into and through the vasculature, establishing an electrical connection between a first lead of an external power source and tissue of the patient to electrically connect the tissue with the external power source, electrically connecting a second lead of the external power source to an electrical connection assembly included within a handle of the medical apparatus, establishing electrical contact between the guidewire and cardiac tissue, establishing electrical contact between the guidewire and the electrical connection assembly of the medical apparatus to electrically connect the cardiac tissue with the external power source, and electrically stimulating the heart with the external power source.

The foregoing and other objects, features, and advantages of the disclosed technology will become more apparent from the following detailed description, which proceeds with reference to the accompanying figures.

DETAILED DESCRIPTION

General Considerations

Figure 1:
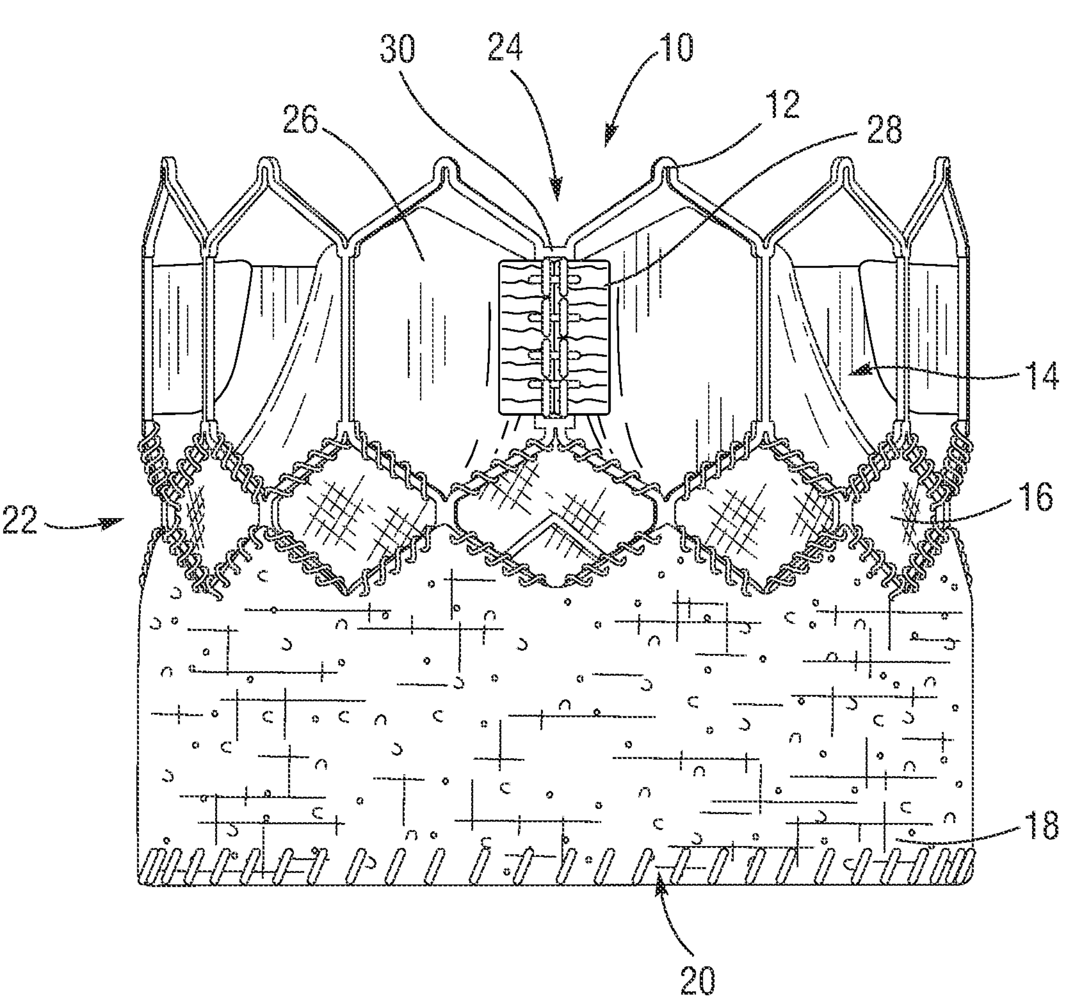
FIG. 1 is a perspective view of a prosthetic heart valve, according to one example.

For purposes of this description, certain aspects, advantages, and novel features of the examples of this disclosure are described herein. The described methods, systems, and apparatus should not be construed as limiting in any way. Instead, the present disclosure is directed toward all novel and non-obvious features and aspects of the various disclosed examples, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing examples. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms “a,” “an,” and “at least one” encompass one or more of the specified element. That is, if two of a particular element are present, one of these elements is also present and thus “an” element is present. The terms “a plurality of” and “plural” mean two or more of the specified element.

As used herein, the term “and/or” used between the last two of a list of elements means any one or more of the listed elements. For example, the phrase “A, B, and/or C” means “A,” “B,” “C,” “A and B,” “A and C,” “B and C,” or “A, B, and C.”

As used herein, the term “coupled” generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as “inside,” “outside,”, “top,” “down,” “interior,” “exterior,” and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an “upper” part can become a “lower” part simply by turning the object over. Nevertheless, it is still the same part and the object remains the same. As used herein, “and/or” means “and” or “or,” as well as “and” and “or”.

As used herein, with reference to the medical apparatus and/or components thereof, “proximal” refers to a position, direction, or portion of the medical apparatus and/or component thereof that is closer to the user and/or a handle of the medical apparatus that is outside the patient, while “distal” refers to a position, direction, or portion of the medical apparatus and/or component thereof that is further away from the user and/or the handle of the delivery apparatus and closer to the implantation site (e.g., native heart valve). The terms “longitudinal” and “axial” refer to an axis extending in the proximal and distal directions, unless otherwise expressly defined. Further, the term “radial” refers to a direction that is arranged perpendicular to the axis and points along a radius from a center of an object (where the axis is positioned at the center, such as the longitudinal axis of the prosthetic valve).

Overview of the Disclosed Technology

The present disclosure relates generally to assemblies, apparatuses, and methods for electrically stimulating a patient’s body. More specifically, the present disclosure relates to assemblies, apparatuses, and methods for electrically stimulating a heart, such as during repair and/or replacement of a native heart valve (e.g., valvuloplasty, transcatheter aortic valve implantation (TAVI), etc.). The assemblies, apparatuses, and methods of the present disclosure allow a physician to more safely and easily electrically stimulate the patient’s tissue during a medical procedure.

Specifically, the handle of the medical apparatuses of the present disclosure may maintain electrical contact between a guidewire and the electrical stimulating device when the guidewire and the medical apparatuses move relative to one another, allowing a physician to conveniently reposition the guidewire and/or medical apparatuses during the medical procedure without severing and/or otherwise sacrificing the integrity of the electrical connection between the guidewire and the electrical stimulation generator (e.g., pacing device). In one example, the handle may include an electrical connection assembly that is configured to establish and maintain an electrical connection between the electrical stimulation generator and the guidewire even when the guidewire and the handle move (e.g., slide) relative to one another. For example, the handle may include a biasing mechanism (e.g., spring) and/or a retention mechanism (e.g., support rod) that urge and/or hold an electrical contacting structure of the electrical connection assembly in electrical contact with the guidewire, allowing the guidewire to move relative to the handle without losing its electrical connection to (i.e., disconnecting from) the electrical stimulation generator.

Further, the handle may provide a self-contained and/or sealed electrical connection between the guidewire and the lead of the electrical stimulation generator, thereby reducing and/or eliminating safety risks to physicians and other medical personnel. As one example, the housing of the handle may at least partially and/or fully enclose and/or seal the electrical connection assembly, the lead of the electrical stimulation generator, and/or the guidewire, thereby minimizing the exposure of these current-carrying components of the electrical stimulation system.

Figure 2:
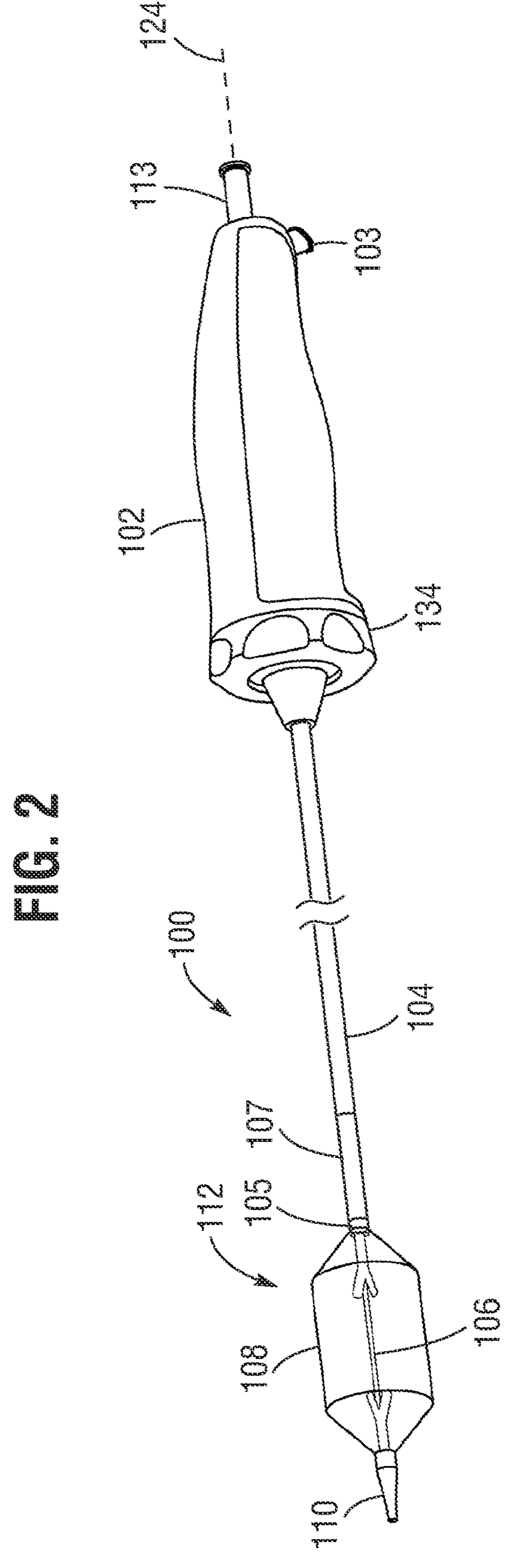
FIG. 2 is a perspective view of a delivery apparatus for implanting a prosthetic heart valve within a native heart valve, according to one example.
Figure 3:
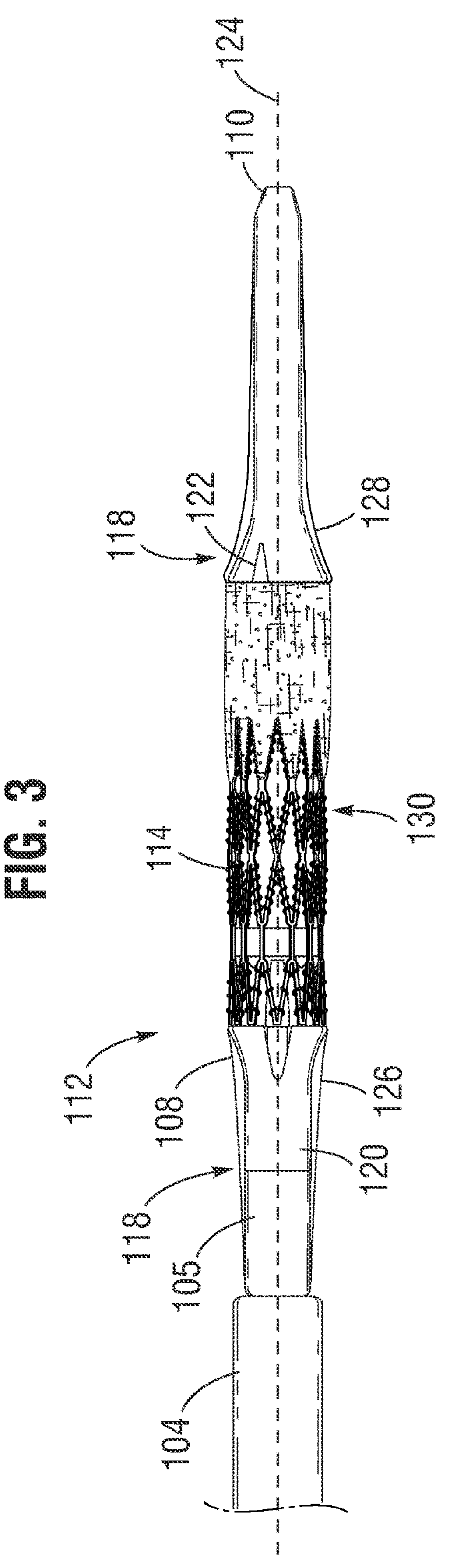
FIG. 3 is an enlarged, cross-sectional view of the distal end portion of the delivery apparatus of FIG. 2 with an exemplary prosthetic heart valve mounted thereon.
Figures 4, 5:
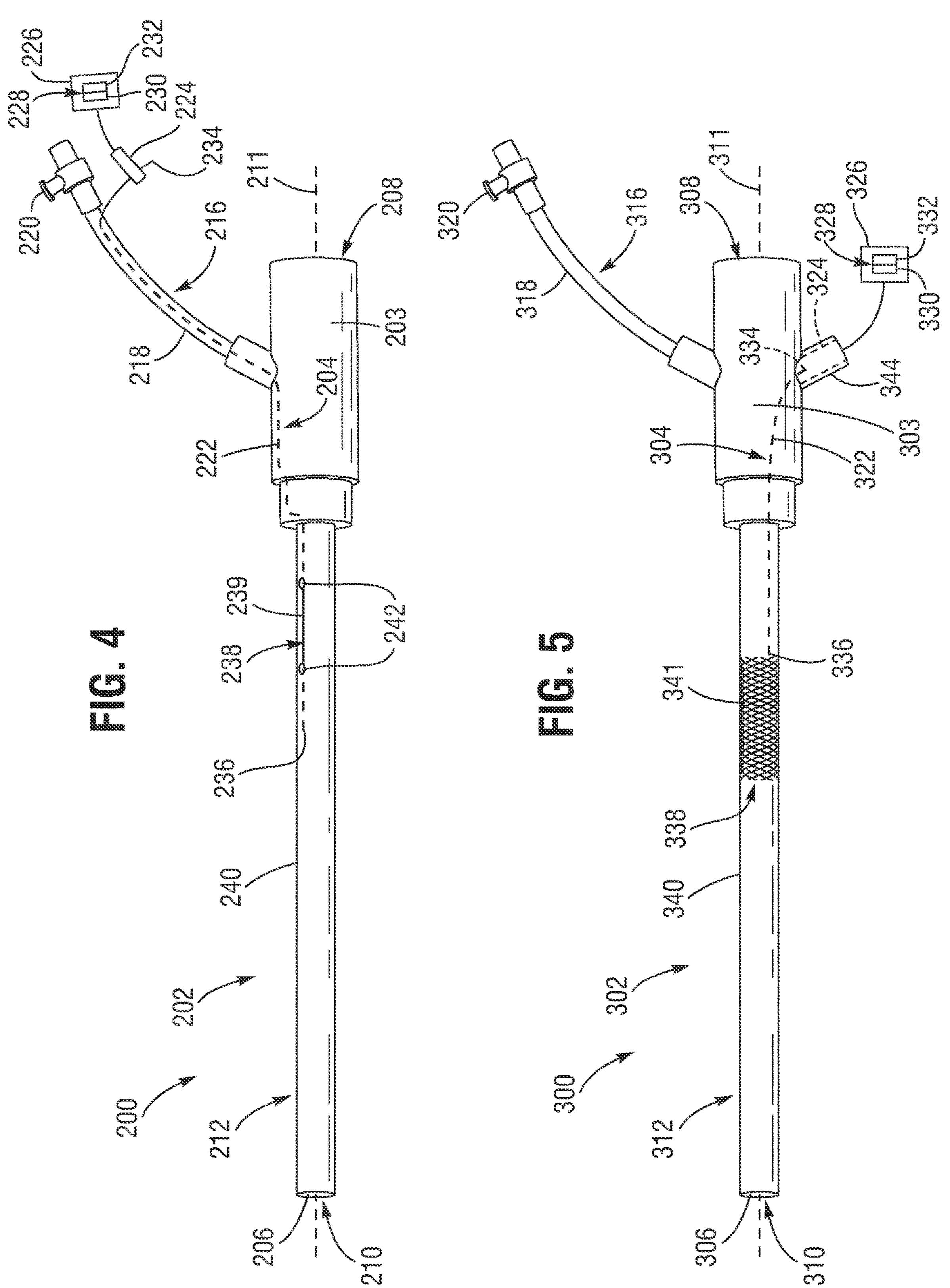
FIG. 4 is a perspective view of an introducer device, according to one example.
FIG. 5 is a perspective view of an introducer device, according to one example.

FIGS. 1-3 depict assemblies, medical apparatuses, devices, and/or components thereof that may be used during various medical procedures that involve electrically stimulating the heart, such as valvuloplasty and heart valve replacement (e.g., TAVI) procedures. Specifically, FIG. 1 depicts an exemplary prosthetic heart valve that may be used to replace a native heart valve, and FIGS. 2-3 depict an exemplary medical apparatus (e.g., endovascular delivery device and/or catheter) that may be inserted into a patient to perform a medical procedure (e.g., valvuloplasty) and/or to deliver a device or instrument, such as the exemplary prosthetic heart valve of FIG. 1, to the patient’s heart. FIGS. 4-5 depict exemplary introducer devices that may be initially implanted in a patient to facilitate subcutaneous insertion of one or more medical assemblies, apparatuses, and/or devices, such as those depicted in FIGS. 1-3. FIGS. 6-10 depict exemplary medical apparatus handles that may be included in a medical apparatus (e.g., catheter), such as the medical apparatus shown in FIG. 2-3, to electrically connect an electrical stimulation generator to a guidewire that is positioned within the patient’s vasculature. By electrically connecting the guidewire to the electrical simulation generator, the guidewire can serve as a first electrode. Additionally or alternatively, one or more of the exemplary introducer devices shown in FIGS. 4-5 may be electrically connected to the electrical stimulation generator to serve as a second electrode.

Figure 10:
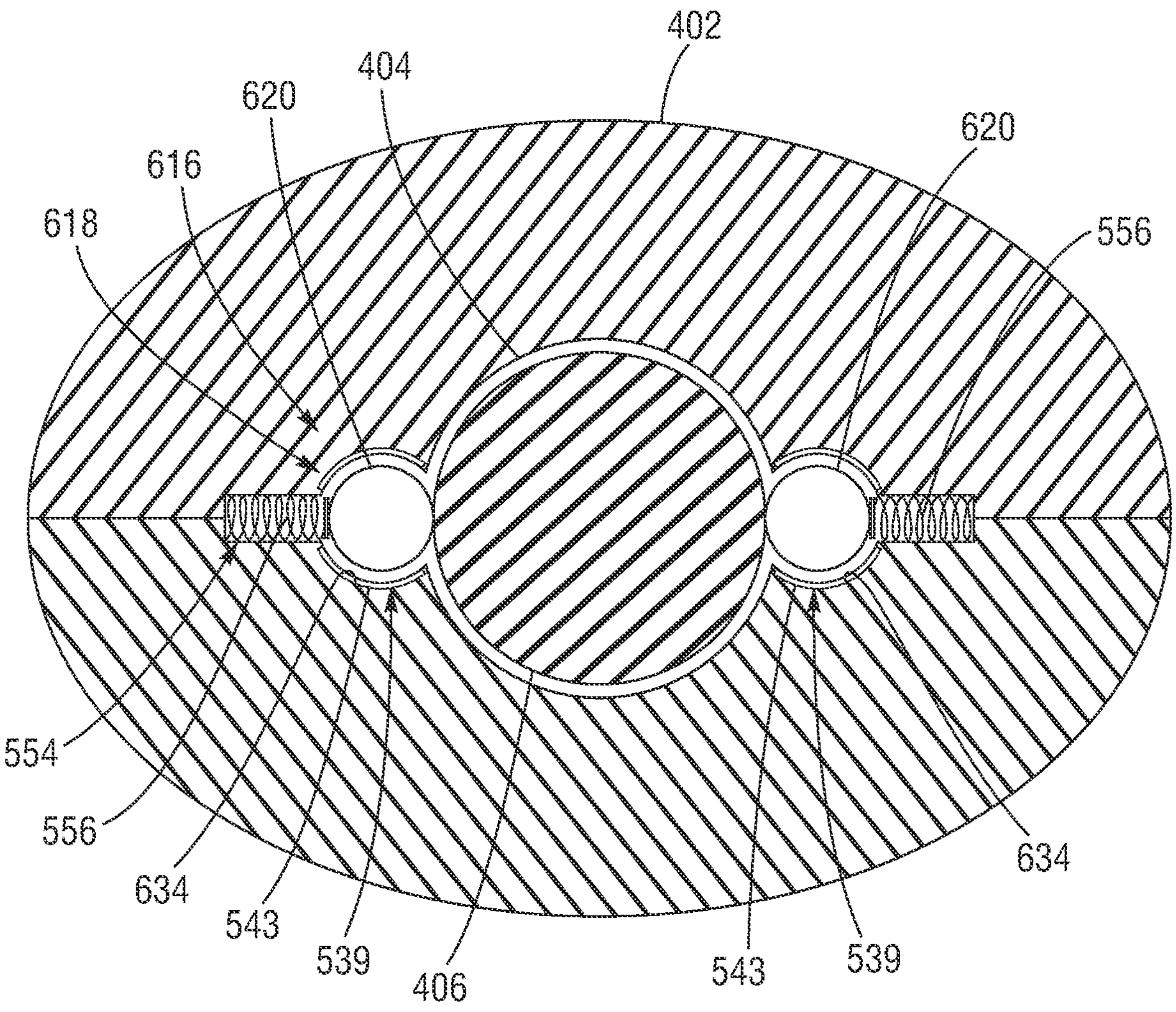
FIG. 10 is a cross-sectional view of the handle of FIG. 6 taken along cutting plane B-B, according to one example.
Figure 11:
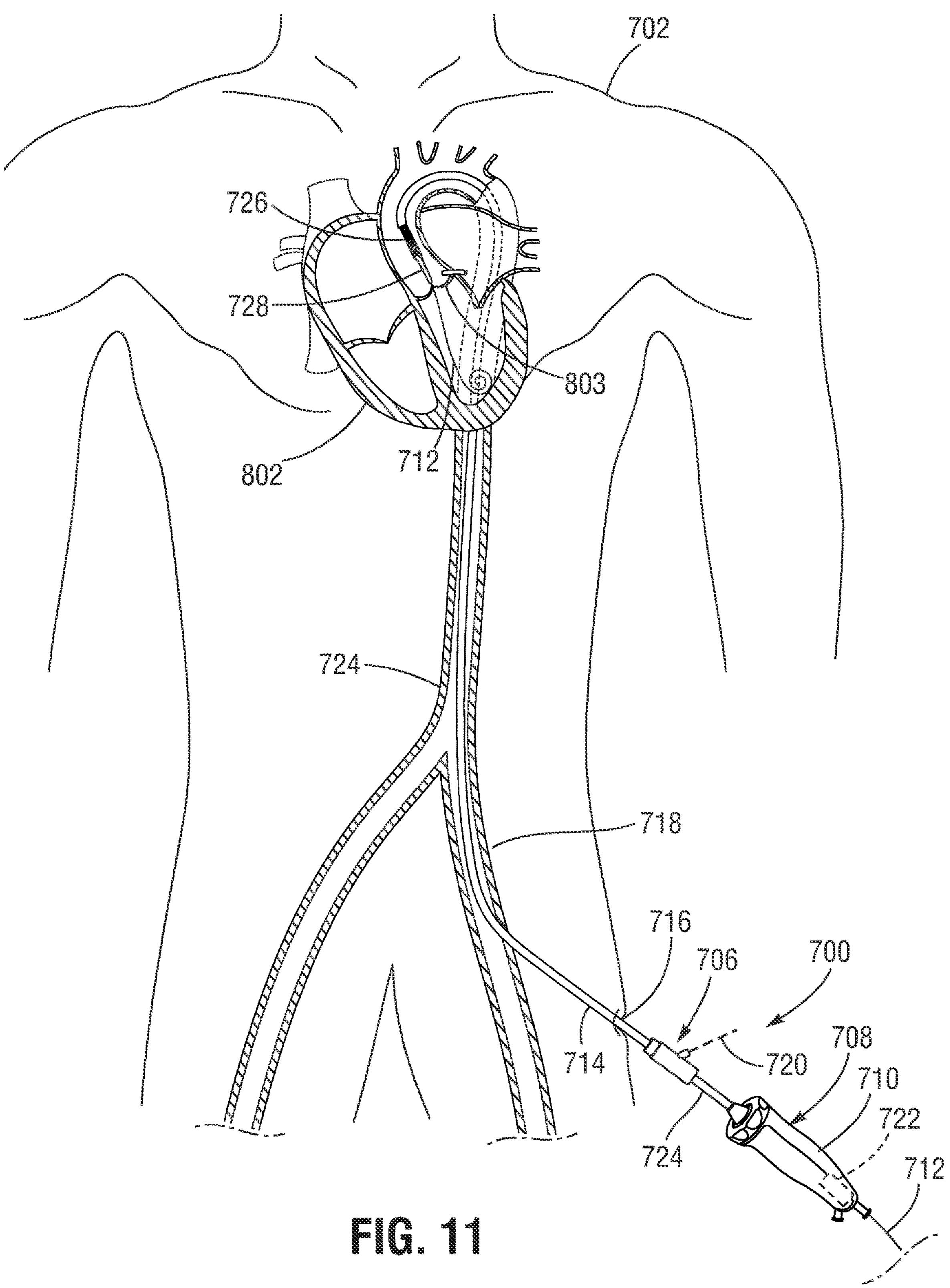
FIG. 11 is a schematic illustration of a medical assembly for rapidly pacing a heart shown extending into a patient's heart during a transcatheter heart valve replacement procedure, according to one example.
Figure 12:
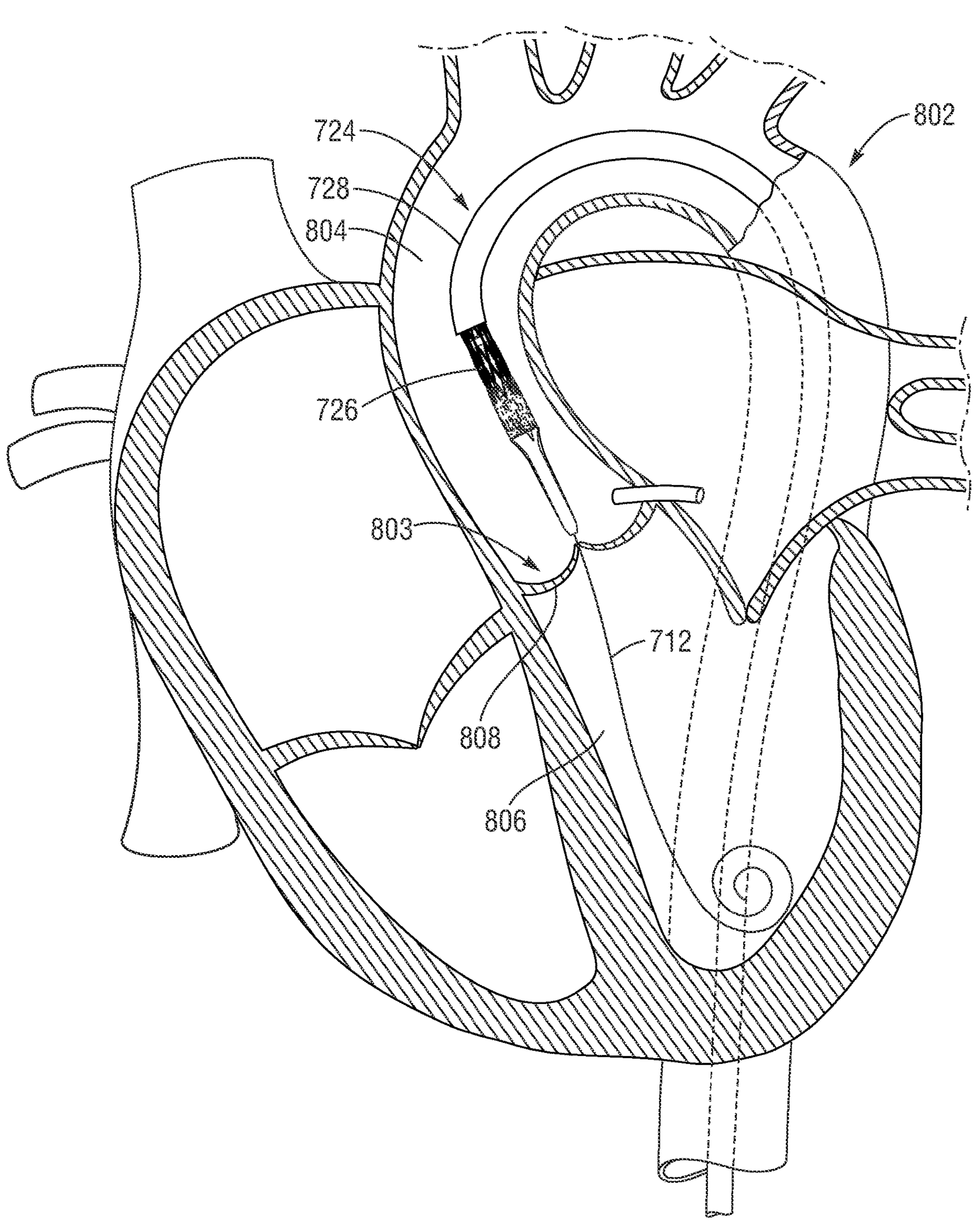
FIG. 12 is an enlarged schematic illustration of a distal end of the medical assembly of FIG. 11 shown extending into the patient's heart with a prosthetic heart valve mounted thereon, according to one example.

FIGS. 11-12 depict an exemplary heart valve replacement procedure (e.g., TAVI procedure) that may employ an introducer device (e.g., one or more of the introducer devices shown in FIGS. 4-5), a medical apparatus (e.g., medical apparatus shown in FIGS. 2-3) having a handle (e.g., one or more of the medical apparatus handles shown in FIGS. 6-10), and a prosthetic heart valve (e.g., prosthetic heart valve shown in FIG. 1). In some examples, one or more of the exemplary introducer devices and/or exemplary medical apparatus handles of the present disclosure may be used to rapidly pace the heart during the heart valve replacement procedure (e.g., TAVI procedure). In particular, a physician may rapidly pace the heart with one of the exemplary introducer devices described herein and/or with a guidewire that is electrically connected to an electrical stimulation generator via one of the exemplary electrical connection assemblies described herein that is included in the handle of the medical apparatus.

During the valve replacement procedure, a physician may initially insert a guidewire and/or introducer device into a patient's vasculature. The introducer device may facilitate the subcutaneous insertion of other devices (e.g., guidewires, delivery devices, catheters, prosthetic heart valves, etc.) into the patient's vasculature, and the guidewire may guide these devices through the patient's vasculature to help prevent them from perforating the walls of the blood vessels and/or other vasculature tissue in route to the heart. After inserting the guidewire and introducer device, the physician may advance a medical apparatus (e.g., endovascular delivery device and/or catheter) containing a distally mounted prosthetic heart valve through the introducer device, over the guidewire, and into the patient's vasculature. The physician may continue to advance the medical apparatus through the patient's vasculature until the prosthetic heart valve (which is crimped on the medical apparatus at and/or near the distal end of the medical apparatus) is positioned near the native valve (e.g., the aortic valve). Once the prosthetic heart valve is near the native valve annulus, the physician may rapidly pace the heart to hold open the native valve while positioning, expanding, implanting, and/or otherwise deploying the prosthetic heart valve within the native heart valve annulus.

As explained above, during conventional heart valve replacement procedures, this rapid pacing is achieved by advancing a separate pacing wire extending through the patient's vasculature into the heart alongside the guidewire, or by attaching a lead of the electrical stimulation generator to a proximal end of the guidewire. However, exemplary methods of the present disclosure may include establishing an electrical connection between the guidewire and a lead of an electrical simulation generator (e.g., pacing device) via the electrical connection assembly of the handle of the medical apparatus. For example, the physician may electrically connect a first lead of the electrical stimulation generator to the electrical connection assembly included within the handle of the medical apparatus. The electrical connection assembly in turn may establish an electrical connection with the guidewire via an electrical contacting structure that may directly physically contact the guidewire. In some examples, methods of the present disclosure may further include electrically connecting a second lead of the electrical stimulation generator to the introducer device. Thus, the introducer device and the guidewire may be electrically connected to the patient's body as well as to the electrical stimulation generator. In this way, the introducer device and the guidewire provide a pathway for current to flow through the patient's body, thereby allowing the electrical simulation generator to rapidly pace and/or otherwise electrically stimulate the patient's heart.

FIG. 1 shows a prosthetic heart valve 10 (also referred to herein as "prosthetic valve 10"), according to one example. The illustrated prosthetic valve is adapted to be implanted in the native aortic annulus, although in other examples it can be adapted to be implanted in the other native annuluses of the heart (e.g., the pulmonary, mitral, and tricuspid valves). The prosthetic valve can also be adapted to be implanted in previously implanted prosthetic valves and other tubular organs or passageways in the body. The prosthetic valve 10 can have four main components: a stent or frame 12, a valvular structure 14, an inner skirt 16, and a perivalvular outer sealing member or outer skirt 18. The prosthetic valve 10 can have an inflow end portion 20, an intermediate portion 22, and an outflow end portion 24.

The valvular structure 14 can comprise three leaflets 26, collectively forming a leaflet structure, which can be arranged to collapse in a tricuspid arrangement, although in other examples there can be greater or fewer number of leaflets (e.g., one or more leaflets 26). The leaflets 26 can be secured to one another at their adjacent sides to form commissures 28 of the valvular structure 14. The lower edge of valvular structure 14 can have an undulating, curved scalloped shape and can be secured to the inner skirt 16 by sutures (not shown). In some examples, the leaflets 26 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 12 can be formed with a plurality of circumferentially spaced slots, or commissure windows 30 that are adapted to mount the commissures 28 of the valvular structure 14 to the frame. The frame 12 can be made of any of various suitable plastically-expandable materials (e.g., stainless steel, a cobalt chromium alloy, etc.) or self-expanding materials (e.g., a nickel titanium alloy (NiTi), such as nitinol) as known in the art. When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular examples, frame 12 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. Additional details regarding the prosthetic valve 10 and its various components are described in WIPO Patent Application Publication No. WO 2018/222799, which is incorporated herein by reference.

FIGS. 2-3 show a medical apparatus 100 (which also may be referred to as a "medical device," "delivery apparatus," "delivery device," endovascular delivery device," and/or "catheter"), according to one example. The medical apparatus 100 includes a radially expandable portion (e.g., inflatable balloon) which can be used to perform valvuloplasty or other medical procedures, and/or to expand a prosthetic heart valve (e.g., valve 10) or other types of expandable prosthetic medical devices (such as a stent or graft) in a patient.

In the example depicted in FIG. 2, the delivery device 100 comprises a handle 102, a steerable outer first shaft 104 extending from the handle 102, an intermediate second shaft 105 (see FIG. 3) extending from the handle 102 coaxially through the steerable outer first shaft 104, and an inner third shaft 106 extending from the handle 102 coaxially through the intermediate second shaft 105 and the steerable outer first shaft 104, an inflatable balloon 108 extending from a distal end of the intermediate second shaft 105, and a nosecone 110 arranged at a distal end of the delivery device 100. A distal end portion 112 of the delivery device 100 includes the balloon 108, the nosecone 110, and a balloon shoulder assembly. A prosthetic medical device, such as a prosthetic heart valve may be mounted on a valve-retaining portion of the balloon 108, as described further below with reference to FIG. 3. As described further below, the balloon shoulder assembly is configured to maintain the prosthetic heart valve or other medical device at a fixed position on the balloon 108 during delivery through the patient's vasculature.

As introduced above, the medical apparatus 100 may be configured to be advanced over a guidewire so that the medical apparatus 100 does not perforate the walls of the vasculature and/or other tissue. Thus, the handle 102 may include a proximal port 113 having a lumen that is configured to receive the guidewire. The lumen of the proximal port 113 is in communication with a lumen or internal passageway of the handle 102, which in turn is in communication with a lumen of the inner third shaft 106 and the nosecone 110. In use, the delivery device 100 can be advanced over the guidewire and into a patient's vasculature. The guidewire extends through the lumen of the nosecone 110 and the inner third shaft 106, the passageway of the handle 102, and the lumen of the proximal port 113. During a procedure, the delivery device 100 and the guidewire can be moved (e.g., axially translated) relative to one another in distal and proximal directions. In some examples, the passageway of the handle 102 may be a central passageway that is centered on a central longitudinal axis 124 of the delivery device 100.

As described in greater detail below with reference to FIGS. 6-10, in some examples, the handle 102 may include an electrical connection assembly that is configured to electrically connect the guidewire to an external electrical stimulation generator (e.g., electrical stimulator, pacing device, etc.). Further, the electrical connection assembly may be configured to maintain an electrical connection with the guidewire when the guidewire and the handle 102 move (e.g., axially translate) relative to one another. In this way, a physician can reposition the guidewire and/or the delivery device 100 during the medical procedure without disconnecting the guidewire from the electrical stimulation generator.

The handle 102 can include a steering mechanism configured to adjust the curvature of the distal end portion 107 of the outer first shaft 104. In the illustrated example, for example, the handle 102 includes an adjustment member, such as the illustrated rotatable knob 134, which in turn is operatively coupled to the proximal end portion of a pull wire (not shown). The pull wire extends distally from the handle 102 through the outer first shaft 104 and has a distal end portion affixed to the outer first shaft at or near the distal end of the outer first shaft 104. Rotating the knob 134 is effective to increase or decrease the tension in the pull wire, thereby adjusting the curvature of the distal end portion 107 of the outer first shaft 104 and therefore the distal end portion 112 of the delivery device.

FIG. 3 shows an example of the distal end portion 112 of the delivery device 100. As shown in FIG. 3, the delivery device 100 is configured to mount a prosthetic valve (e.g., prosthetic heart valve) 114 in a crimped state over the balloon 108 for insertion of the delivery device 100 and prosthetic valve 114 into a patient's vasculature.

As shown in FIG. 3, at a proximal end of the distal end portion 112, the inner third shaft 106 extends distally beyond the steerable shaft 104 and the intermediate second shaft 105 and through the balloon 108. The balloon 108 can be supported on a balloon shoulder assembly 118. The balloon shoulder assembly 118 includes a proximal shoulder 120 connected to a distal end of the intermediate second shaft 105 and a distal shoulder 122 mounted on the inner third shaft 106. The balloon 108 includes a proximal end portion 126 surrounding and/or folded over the proximal shoulder 120 and a distal end portion 128 surrounding and/or folded over the distal shoulder 122. In some examples, the proximal end portion 126 of the balloon 108 may be secured to the outer surface of the intermediate second shaft 105. In some examples, the distal end portion 128 of the balloon 108 may be secured to the outer surface of the nosecone 110 (as shown), which can be mounted on or coupled to the inner third shaft 106.

In the illustrated example, the nosecone 110 and the distal shoulder 122 can be a one-piece or unitary component, that is, the nosecone 110 is a distal portion of the unitary component and the distal shoulder 122 is a proximal portion of the unitary component. In other examples, the nosecone 110 and the distal shoulder 122 can be separate components, and each can be mounted on the inner third shaft 106 next to each other or at axially spaced locations.

The proximal shoulder 120 and the distal shoulder 122 are spaced apart from one another, in an axial direction relative to the central longitudinal axis 124 of the delivery device 100. As a result, the balloon 108 defines a valve-retaining portion 130 in the space that separates the proximal shoulder 120 and the distal shoulder 122 (e.g., between flared ends of the proximal shoulder 120 and the distal shoulder 122). As shown in FIG. 3, the prosthetic valve 114 can be crimped onto the valve-retaining portion 130 of the balloon 108, between the proximal shoulder 120 and the distal shoulder 122, thereby preventing or reducing axial movement of the prosthetic valve 114 relative to the balloon 108 during insertion of the delivery device 100 into the patient and delivery of the prosthetic valve 114 to the target implantation site.

The outer diameter of the inner third shaft 106 can be sized such that an annular space is defined between the inner third shaft 106 and the intermediate second shaft 105 along the entire length of the intermediate second shaft 105. The annular space may be fluidly coupled to one or more fluid passageways of the delivery device 100 which can be fluidly connectable to a fluid source (e.g., a syringe) that can inject an inflation fluid (e.g., saline) into the delivery device. In this way, fluid from the fluid source can flow through the one or more fluid passageways, through the annular space between the inner third shaft 106 and the intermediate second shaft 105, and into the balloon 108 to inflate the balloon 108 and expand and deploy the prosthetic valve 114. For example, the handle 102 can have a fluid port 103 (see FIG. 2) configured to be coupled to the fluid source. In use, inflation fluid from the fluid source can be injected into the fluid port 103, through one or more fluid passageways in the handle 102, through the annular space separating the inner third shaft 106 and the intermediate second shaft 105, and into the balloon 108.

The shafts 104, 105, and 106 of the delivery device 100 can be formed from any of various suitable materials, such as nylon, braided stainless steel wires, or a polyether block amide (commercially available as Pebax®), to name a few. The shafts 104, 105, and 106 can have longitudinal sections formed from different materials in order to vary the flexibility of the shafts along their lengths. The inner third shaft 106 can have an inner liner or layer formed of Teflon® to minimize sliding friction with a guide wire. The shafts 104, 105, and 106 can also be axially and/or rotatably movable relative to each other and/or the handle 102.

Further details of the balloon shoulder assembly, the steering mechanism, and other components of the delivery device are disclosed in U.S. Publication Nos. 2007/0005131, 2009/0281619, 2013/0030519, and 2017/0065415, which are incorporated herein by reference.

In some examples, the delivery device 100 need not include a steering mechanism or a shaft 104 (in which case the shaft 105 is the outer shaft of the delivery device). In some examples, the delivery device 100 need not include a shaft 104 and can include a steering mechanism configured to adjust the curvature of the shaft 105 (e.g., the pull wire can extend through the shaft 105).

Examples of the Disclosed Technology

FIGS. 4-5 depict different examples of introducer devices that may be configured to be electrically connected to an external electrical stimulation generator (e.g., pacing device and/or electrical stimulator) to serve as an electrode. Like conventional introducer devices, the exemplary introducer devices depicted in FIGS. 4-5 may initially be inserted into the patient to facilitate the subsequent subcutaneous insertion of one or more medical apparatuses, devices, and/or instruments (e.g., medical apparatus 100). Thus, once the introducer device is implanted in the patient, a medical apparatus (e.g., endovascular delivery device), such as medical apparatus 100 described above, may be advanced through the introducer device into the patient's vasculature.

However, in addition to this traditional functionality, the exemplary introducer devices depicted in FIGS. 4-5 also may be configured to serve as one of the electrodes for the external electrical stimulation generator. In particular, the introducer devices of the present disclosure may include an electrical connection assembly that is configured to be electrically connected to the patient's tissue and to a lead of the external electrical stimulation generator to electrically connect the external electrical stimulation generator to the patient's tissue. FIG. 4 depicts a first example of this electrical connection assembly where an exposed portion of an electrically conductive wire is configured to electrically connect to the patient's tissue, whereas FIG. 5 depicts another example of this electrical connection assembly in which a metal braid is configured to electrical connect to the patient's tissue.

By serving as an electrode for the external electrical stimulation generator, the introducer devices of the present disclosure may eliminate the need to attach a separate, external component (e.g., alligator clip, needle, etc.) to the skin or tissue of the patient near the insertion site. Instead, the introducer device's generally enclosed structure can be leveraged to provide a less exposed, better sealed, and therefore safer electrical connection between the electrical stimulation generator and the patient's tissue. Further, incorporating the electrode within the introducer device reduces the total number of separate components used during the medical procedure, thereby simplifying and streamlining the medical procedure.

FIG. 4 depicts an introducer device 200, according to one example. Introducer device 200 comprises a sheath 202 (which also may be referred to herein as "shaft 202"), a proximal hub or housing 203, and an electrical connection assembly 204. The sheath 202 extends distally from the housing 203. The sheath 202 and the housing 203 define a lumen 206 (which also may be referred to herein as "passageway 206" and/or "hollow internal passageway 206). The lumen 206 extends along the entire length of the introducer device 200, from a proximal end 208 of the housing 203 to a distal end 210 of the sheath 202, and is configured to receive a medical apparatus (e.g., medical apparatus 100), guidewire, and/or other devices. Thus, the medical apparatus, guidewire, and/or other devices may be extended through the lumen 206 of the introducer device 200 into, for example, a patient's vasculature. In some examples, the lumen 206 may be centered on a central longitudinal axis 211 of the sheath 202 and thus also may be referred to herein as "central passageway 206."

The sheath 202 comprises a distal portion 212 that is configured to be extended into the vasculature of a patient while the housing 203 is configured to remain outside the patient to facilitate the subcutaneous insertion of the medical apparatus, guidewire, and/or other devices. The housing 203 can house one or more elastomeric seals (e.g., slit seals or cross seals) configured to contact and establish a fluid seal with an outer surface of a medical apparatus that is inserted through the introducer device 200. In certain examples, the sheath 202 can be radially expandable once inserted into a patient's vasculature to more easily accommodate a medical apparatus (e.g., a delivery apparatus and prosthetic valve) that is inserted through the introducer device. For example, the sheath 202 can be configured to radially expand as the medical apparatus is inserted through the sheath as a result of the outward force of the medical apparatus against the inner surface of the sheath, such as disclosed in U.S. Pat. No. 8,790,387 and U.S. Publication No. 2019/0307589, which are incorporated herein by reference.

In some examples, the introducer device 200 includes a fluid port 216 that is configured to provide flushing fluid to the lumen 206 of the shaft 202 to prevent blood clot formation (i.e., thrombosis). The fluid port 216 may include a fluid conduit 218 that is connected to the housing 203 and a flow control mechanism 220, such as a knob, wheel, button, or other adjustable member, that is configured to be adjusted to control the flow of the flushing fluid to the lumen 206 of the shaft 202.

In the example depicted in FIG. 4, the electrical connection assembly 204 extends through the fluid port 216. Specifically, the electrical connection assembly 204 comprises an electrically conductive wire 222 that extends through the fluid port 216. In some examples, the electrically conductive wire 222 may include an electrically insulating cover that protects the electrically conductive wire 222 from liquids that may be present in the fluid port 216 and/or the lumen 206 of the shaft 202. Electrically conductive wire 222 may have a proximal end portion that extends out of the fluid port 216 (e.g., through a sealed opening in the fluid port 216), and thus out of the introducer device 200, so that is accessible to users (e.g., medical personnel) on the outside of the patient. In this way the electrically conductive wire 222 can be connected to a lead 224 of an external electrical stimulation generator 226 (which also may be referred to herein as "pacing device," and "electrical stimulator 226"), such as by clamping, attaching, and/or otherwise removably coupling the lead 224 to the electrically conductive wire 222. The lead 224 of the external electrical stimulation generator 226 may in turn be electrically connected to an electric power source 228 (e.g., battery) of the external electrical stimulation generator 226, and more specifically, to a first electrode 230 of the external electrical stimulation generator 226. The electrical stimulation generator 226 comprises the first electrode 230 and a second electrode 232 that have opposite polarities. As one example, the first electrode 230 may be an anode and the second electrode 232 may be a cathode. However, in other examples, the first electrode 230 may be a cathode and the second electrode 232 may be an anode.

The electrical stimulation generator 226 is configured to provide electrical stimulation (e.g., an electric pulse) to tissue (e.g., to the heart) of a patient when electrically connected to the patient's tissue. Specifically, the lead 224 of the external electrical stimulation generator 226 may be configured to be coupled (e.g., via a clip or other suitable attachment mechanism) to the portion of the electrically conductive wire 222 that extends outside the introducer device 200. The electrical stimulation generator 226 may further include a processor that is configured to regulate the current and/or voltage provided by the electric power source 228.

The electrically conductive wire 222 comprises a proximal end portion 234 that extends outside of the introducer device 200 and a distal end portion 236 that extends at least partially into the shaft 202 of the introducer device 200. In some examples, the electrically conductive wire 222 may be coupled to the lead 224 at and/or near the proximal end portion 234 of the electrically conductive wire 222. The electrically conductive wire 222 may extend from the proximal end 234 through the fluid conduit 218 of the fluid port 216, the housing 203, and into shaft 202. In some examples, the wire 222 can be disposed or encapsulated within the walls of the conduit 218, the housing 203, and/or the shaft 202 to avoid contact with fluids in the introducer device and/or medical devices inserted through the introducer device.

However, a portion of the electrically conductive wire 222 may extend outside the shaft 202 to establish an electrical connection with tissue of the patient. In particular, the electrical connection assembly 204 may comprise an electrical contacting structure 238 which, in the example depicted in FIG. 4, comprises an exposed portion 239 of the electrically conductive wire 222 that extends outside the shaft 202, that is configured to electrically contact and/or connect to the patient's tissue. Specifically, the electrical contacting structure 238 may be configured to physically contact the patient's tissue and/or to be positioned close enough to the patient's tissue and/or biological fluid to readily conduct electric current between the patient's tissue and the electrically conductive wire 222. In this way, the electrical contacting structure 238 may serve as an electrode (e.g., anode) for the external electrical stimulation generator 226 and may provide an electrical connection between the electrical stimulation generator 226 and the patient's tissue.

As noted above, in the example depicted in FIG. 4, the electrical contacting structure 238 comprises the exposed portion 239 of the electrically conductive wire 222. The shaft 202 may correspondingly include one or more openings 242 that are configured to permit the exposed portion 239 of the electrically conductive wire 222 to extend outside of the distal portion 212 of the shaft 202. Thus, the exposed portion 239 of the electrically conductive wire 222 may protrude out of the shaft 202 through the one or more openings 242 and may extend along the external surface 240 of the shaft 202. In this way, the exposed portion 239 may be configured to establish an electrical connection with the tissue of a patient.

The exposed portion 239 of the electrically conductive wire 222 may not include the electrically insulating cover so that the exposed portion 239 can readily conduct current with the surrounding tissue. Thus, in some examples, only the internal portions of the electrically conductive wire (the portions of the electrically conductive wire 222 contained within and/or inside the shaft 202 of the introducer device 200 (e.g., within the lumen 206 of the shaft 202)) and/or at least some of the portion of the electrically conductive wire 222 that extends outside the fluid port 216 may be covered with the electrically insulating material. In this way, aside from the exposed portion 239, the electrically conductive wire 222 may be electrically shielded by the electrically insulating cover, thus providing a safer connection between the external electrical stimulation generator 226 and the patient's tissue.

FIG. 5 depicts an introducer device 300, according to another example. In the example of FIG. 5, the electrical contacting structure may comprise a metal braid instead of an exposed portion of the electrically conductive wire like in the example of FIG. 4. That said, the introducer device 300 may comprise one or more components that are generally similar to one or more components of the introducer device 200. Thus, for conciseness, the components of the introducer device 300 that are similar to the components of the introducer device 200 are labeled similarly and may not include additional description. For example, the introducer device 300 comprises a shaft 302, a housing 303, a lumen 306 extending from a proximal end 308 and to a distal end 310, an electrical connection assembly 304 that is configured to be electrically connected to an external electrical stimulation generator 326, and optionally includes a fluid port 316 (corresponding to the shaft 202, lumen 206, proximal end 208, distal end 210, electrically connection assembly 204, external electrical stimulation generator 226, and fluid port 216 of introducer device 200).

In the example depicted in FIG. 5, the electrical contacting structure 338 comprises a metal braid 341. The metal braid 341 may extend over, cover, be coupled to, and/or otherwise be included on the external surface 340 of the shaft 302. The metal braid 341 may be electrically connected to the electrically conductive wire 322 (e.g., via direct physical contact and/or via one or more intermediate electrically conductive elements). For example, the distal end 336 of the electrically conductive wire 322 may directly physically contact the metal braid 341 and/or may extend on an internal surface of the shaft 302 (a surface that is opposite the external surface 340) in a region of the shaft where the metal braid 341 is included. In some examples, the metal braid may be included on only a portion of the external surface 340 of the shaft 302. In some such examples, the metal braid 341 may extend around the entire shaft 302 (e.g., around a circumference of the shaft 302 when viewed in a plane orthogonal to the longitudinal axis 311), but only along a portion of the length of the shaft 302. However, in other examples, the metal braid 341 may extend along the entire length of the shaft 302, and/or may not extend entirely around the shaft 302. In some examples, the metal braid 341 can be a radially expandable metal braided layer of the shaft that can radially expand as a delivery apparatus is inserted through the introducer device, as disclosed in U.S. Publication No. 2019/0307589.

Further, in the example depicted in FIG. 5, the electrical connection assembly 304 comprises a dedicated electrical socket 344 for the lead 324 of the external electrical stimulation generator 326. The electrical socket 344 may be configured to removably couple to the lead 324 of the external electrical stimulation generator 326 to provide an electrical connection between the electrical connection assembly 304 and the external electrical stimulation generator 326. Instead of extending through the fluid port 316, the proximal end 334 of the electrically conductive wire 322 may be coupled and/or otherwise electrically connected to the electrical socket 344. Thus, in the example depicted in FIG. 5, the electrically conductive wire 322 may not extend outside of the introducer device 300 and may be fully contained within the device 300.

As depicted in the example of FIG. 5, the electrical socket 344 may be included on an exterior of the housing 303. Thus, the electrical socket 344 may be configured to be located outside of the patient so that it is easily accessible to medical personnel. By including the electrical socket 344, the introducer device 300 may provide a more sealed, and thus safer, electrical connection between the lead 324 of the external electrical stimulation generator 326 and the electrically conductive wire 322.

Although FIGS. 4-5 depict specific examples of the introducer devices of the present disclosure, it should be appreciated that components of the introducer devices 200 and 300 may be altered, varied, and/or used in different combinations than those shown in FIG. 4-5. For example, although the electrically conductive wire 222 is depicted as extending through the fluid port in FIG. 4, it should be appreciated that the introducer device 200 may alternatively include an electrical socket like the introducer device 300, and the electrically conductive wire 222 may instead extend to the electrical socket. As another example, the introducer device 300 depicted in FIG. 5 may not include a dedicated electrical socket for the lead 324 of the external electrical stimulation generator 326, and the electrically conductive wire 322 may instead extend through the fluid port 316 like in the example of FIG. 4.

Further, although FIGS. 4-5 depict the electrical contacting structure as comprising either an exposed portion of the electrically conductive wire (FIG. 4) or a metal braid (FIG. 5), it should be appreciated that other electrically conductive materials and/or arrangements of electrically conductive materials may be included on the external surface of the shaft of the introducer device to establish an electrical connection with the tissue of the patient. As just one example, the electrical contacting structure may comprise an electrically conductive metal that is arranged on the external surface of the shaft in a non-braided pattern.

The introducer devices 200 and 300 can be used to perform rapid pacing by electrically connecting one of the electrodes of a generator 226, 326 to the wire 222, 322 of the introducer. The other electrode of the generator 226, 326 can be electrically connected to a guidewire extending through the patient's vasculature and having a distal end portion in contact with tissue of the heart. Typically, the anode 230, 330 is electrically connected to the wire 222, 322 of the introducer and the cathode 232, 332 is electrically connected to the guidewire. The guidewire can be a guidewire that is used to advance a medical apparatus (e.g., a valve delivery apparatus) into the patent's vasculature, or a guidewire that is separate from the guidewire used to advance the medical apparatus into the patient's vasculature. FIGS. 6-12 disclose devices and methods for rapid pacing wherein the guidewire used for advancing a medical apparatus into the patent's vasculature is electrically connected to an electrode (e.g., the cathode) of a generator.

Figure 6:
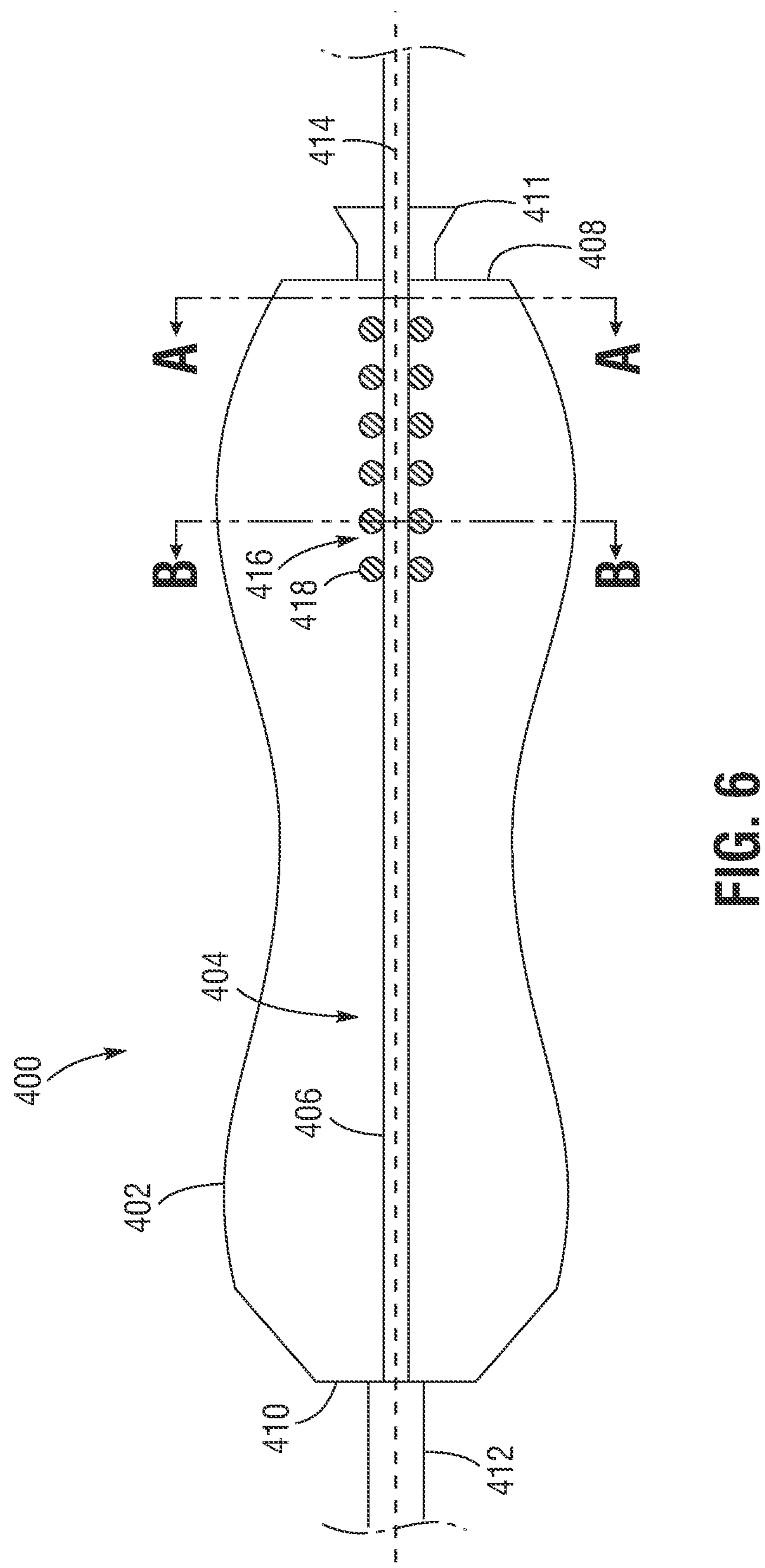
FIG. 6 is schematic top view of a handle of a medical apparatus, such as a delivery apparatus for a prosthetic heart valve, according to one example.

FIG. 6 depicts a handle 400 that may be included in a medical apparatus (e.g., medical apparatus 100), according to one example. Handle 400 includes a housing 402 that has, includes, and/or otherwise defines an internal passageway 404. Internal passageway 404 is configured to receive a guidewire 406 and to permit the guidewire 406 and the handle 400 to move (e.g., axially translate) relative to one another. Thus, the guidewire 406 may extend through the internal passageway 404 and may be configured to move (e.g., slide axially) relative to the handle 400 through the internal passageway 404. In this way, the guidewire 406 may be slidably coupled to the housing 402. In some examples, the internal passageway 404 may extend along an entire length of the handle 400, from a proximal end 408 of the handle 400 to a distal end 410 of the handle 400.

In some examples, the handle 400 may include a locking mechanism 411 that is configured to be selectively adjusted by a user (e.g., medical personnel) to prevent and/or permit axial movement of the guidewire 406 relative to the handle 400. For example, the locking mechanism 411 may be adjusted between a locked position where the locking mechanism 411 prevents relative axial movement between the guidewire 406 and the handle 400 and an unlocked position where the locking mechanism 411 permits the guidewire 406 and the handle 400 to move axially relative to one another. In one such example, the locking mechanism 411 comprises a luer lock. However, in other examples, the locking mechanism 411 may comprise a knob, latch, clamp, or other suitable mechanically adjustable locking structure. In some examples, the locking mechanism 411 also may be configured to provide a fluid seal between the housing 402 of the handle 400 and the guidewire 406. In this way, the locking mechanism 411 may provide a seal between the guidewire 406 and the housing 402, thus increasing the electrical safety of the handle 400 when the guidewire 406 is electrically connected to an external electrical stimulator.

As explained above with reference to FIGS. 2-3, the handle 400 may be coupled to one or more shafts of a medical apparatus (e.g., medical apparatus 100), such as shaft 412. Specifically, the shaft 412 of the medical apparatus may be coupled to the distal end 410 of the housing 402 and may extend distally from the distal end 410 of the housing 402 into, for example a vasculature of a patient. In some examples, the guidewire 406 may extend through the shaft 412 of the medical apparatus in addition to the internal passageway 404 of the handle 400. In particular, the guidewire 406 may extend distally from the proximal end 408 of the handle 400 to the distal end 410 of the handle 400, and out the distal end 410 of the handle 400 into and through the lumen of the shaft 412. In certain examples, the shaft 412 is similar to inner third shaft 106 of FIG. 2, and the medical apparatus can also include the intermediate second shaft 105 and/or the outer first shaft 104.

In some examples, the internal passageway 404 may be centered along a central longitudinal axis 414 of the handle 400. However, in other examples, the internal passageway 404 may be positioned off-center of the central longitudinal axis 414. In yet further examples, the handle 400 may not include an internal passageway for the guidewire 406 and instead may include an external passageway for the guidewire 406 that is located adjacent to the housing 402. For example, the handle 400 may include hooks, loops, and/or other attachment structures on an exterior of the housing 402 that are configured to secure the guidewire 406 to the handle 400 while permitting the guidewire 406 to move relative to the handle 400 (e.g., attachment structures that allow the guidewire 406 to slide relative to the handle 400 along an exterior surface of the housing 402).

As introduced above, handle 400 includes an electrical connection assembly 416 that is configured to electrically connect a lead of an external electrical stimulation generator to the guidewire 406. In this way, a separate pacing wire may not be needed to electrically stimulate a patient's tissue since the guidewire 406 itself (which may comprise a metal or other electrically conductive material) can serve as an electrode for the external electrical stimulation generator. Further, because the electrical connection assembly 416 is configured to maintain the electrical connection between the lead of the external electrical stimulation generator and the guidewire 406 even when the guidewire 406 and the handle 400 move relative to one another, a user may reposition the handle 400 and/or the guidewire 406 during a medical procedure without disconnecting the guidewire 406 from the external electrical stimulation generator. Specifically, the electrical connection assembly 416 may comprise at least one electrical contacting structure 418 that is configured to maintain contact with the guidewire 406 as the guidewire moves longitudinally (i.e., axially) relative to the handle, or vice versa. The electrical contacting structure 418 may be supported on or by an internal wall of the housing 402 and is positioned such that the electrical contacting structure electrically contacts the guidewire 406. As will be explained in greater detail below, the electrical connection assembly may comprise a biasing mechanism and/or a retention mechanism that is/are configured to hold the electrical contacting structure in place and/or maintain the electrical contacting structure in electrical contact with the guidewire 406.

Figure 7:
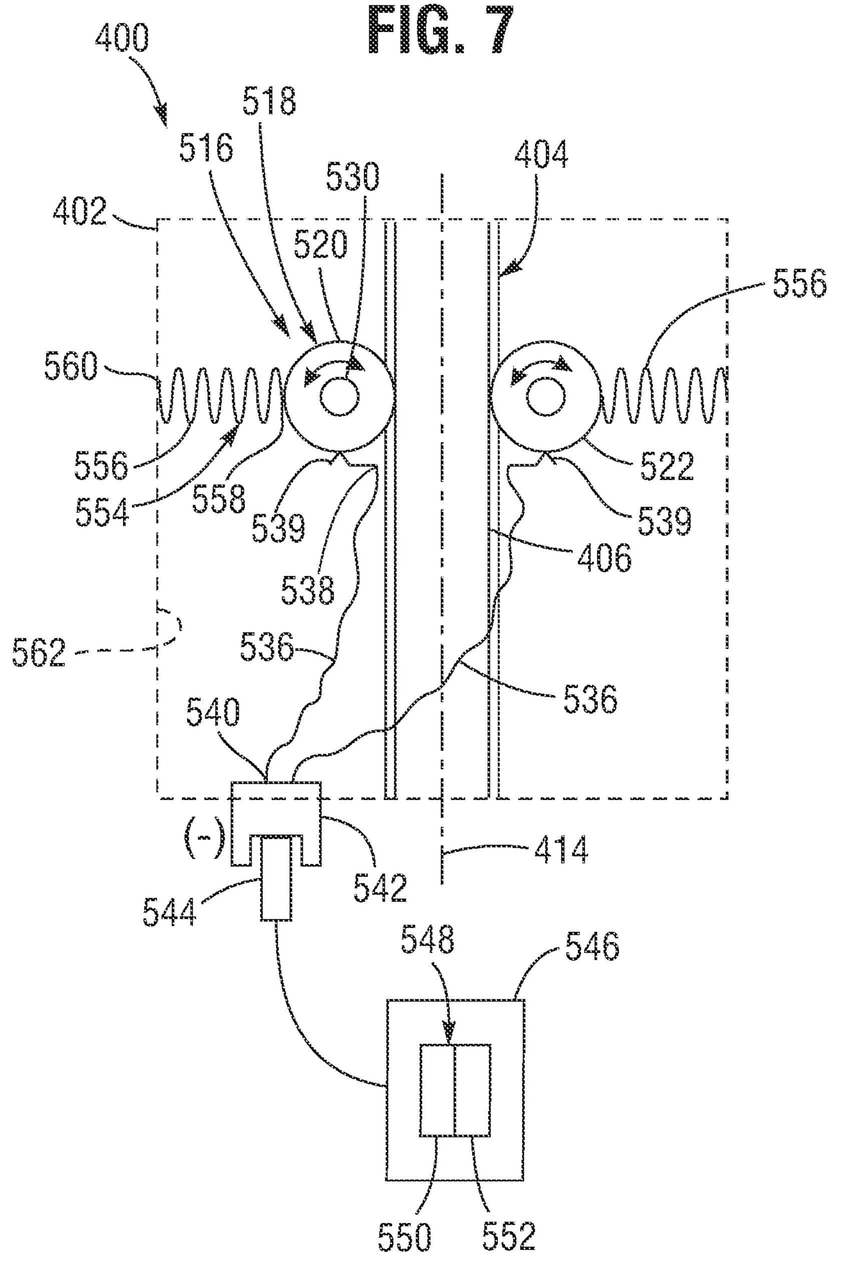
FIG. 7 is an enlarged, schematic illustration of the handle of FIG. 6, according to one example.
Figure 8A:
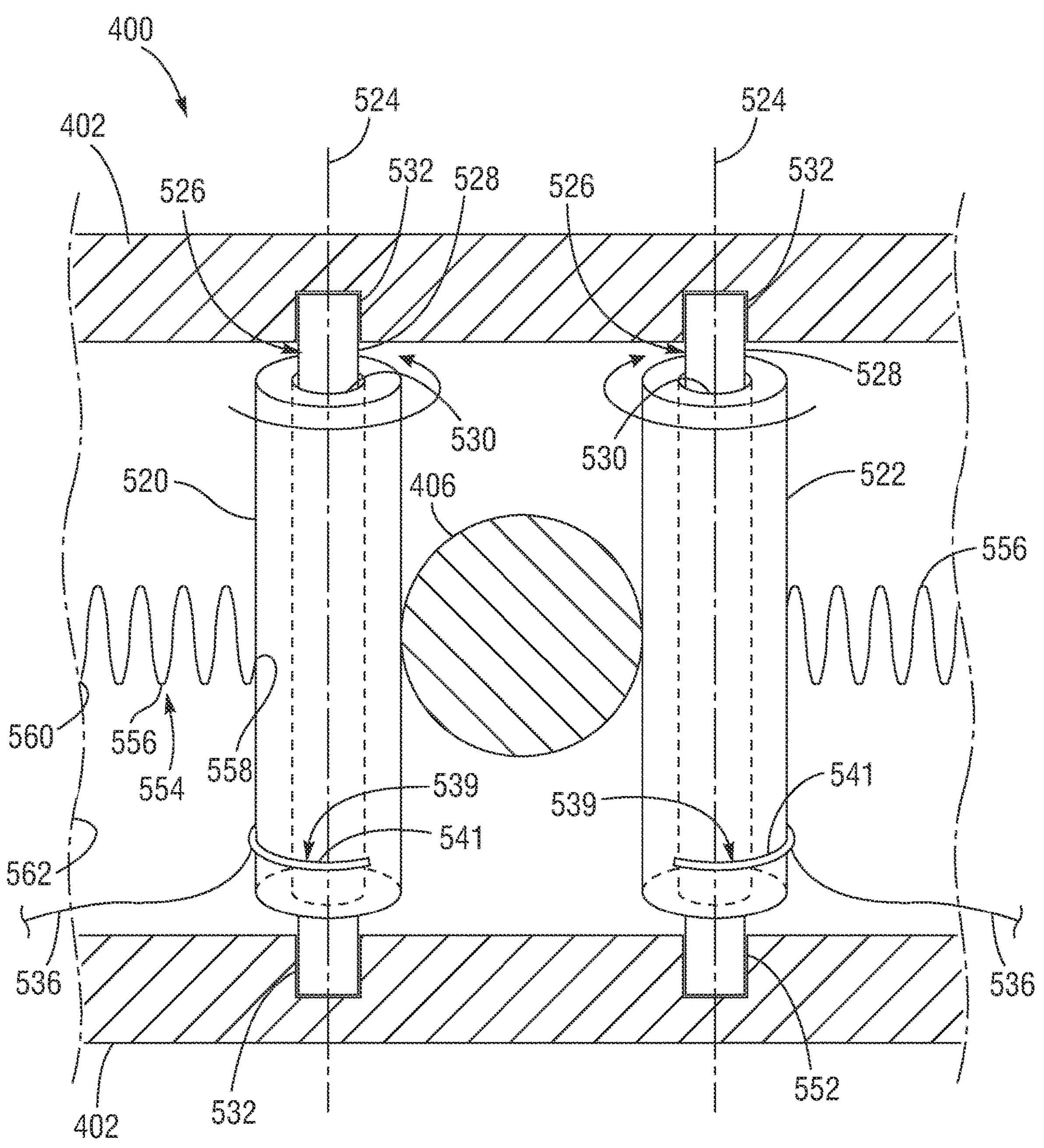
FIG. 8A is a cross-sectional view of the handle of FIG. 6 taken along cutting plane A-A, according to one example.
Figure 8B:
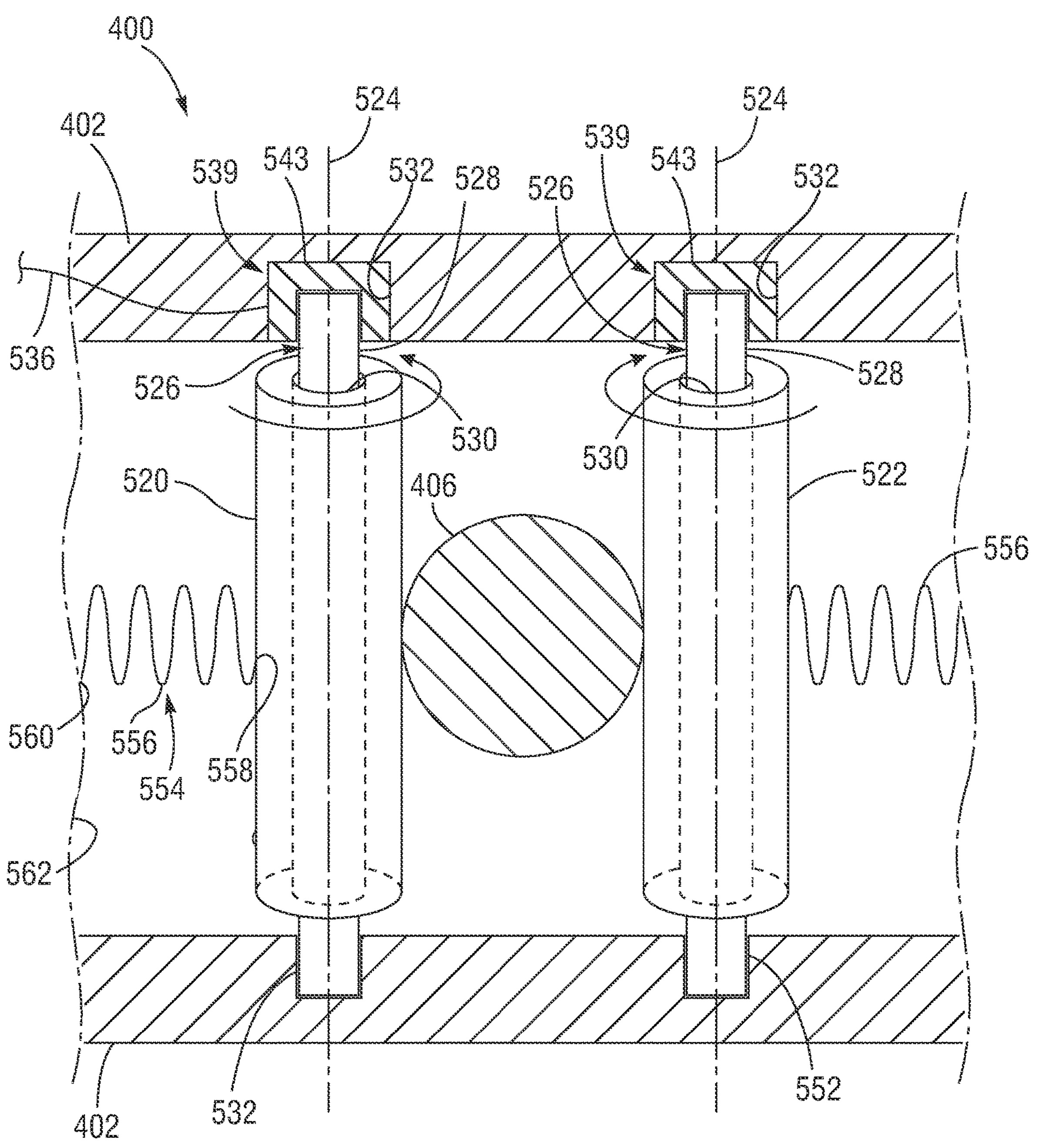
FIG. 8B is a cross-sectional view of the handle of FIG. 6 taken along cutting plane A-A, according to one example.
Figure 9:
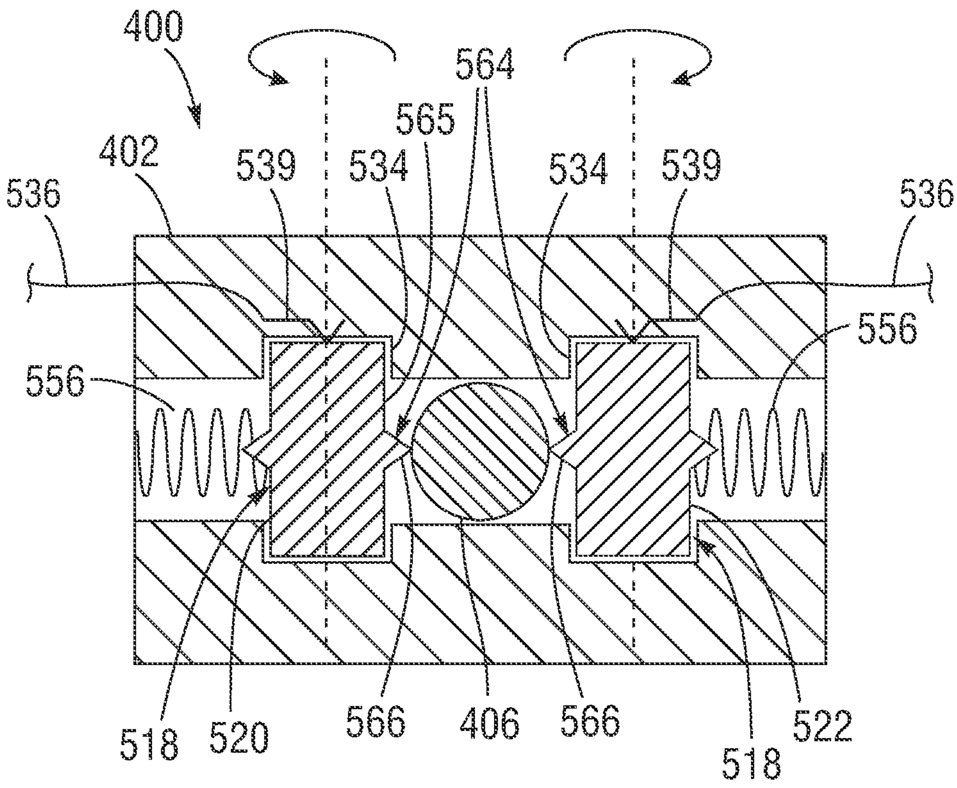
FIG. 9 is a cross-sectional view of the handle of FIG. 6 taken along cutting plane B-B, according to one example.

FIGS. 7-10 depict various examples of electrical connection assemblies that may be included in the handle 400. Specifically, FIGS. 7-9 depict one such example of the handle 400 in which the electrical contacting structure of the electrical connection assembly comprises a cylindrically shaped roller, while FIG. 10 depicts another such example of the handle in which the electrical contacting structure comprises a spherically shaped ball.

FIGS. 7-9 depict various views of the handle 400 of FIG. 6, according to one such example. FIG. 7 is an enlarged, schematic illustration of the handle 400, FIGS. 8A-8B are cross-sectional views of the handle 400 of FIG. 6 taken along cutting plane A-A, and FIG. 9 is a cross-sectional view of the handle of FIG. 6 taken along cutting plane B-B.

In the examples of FIGS. 7-9, handle 400 includes an electrical connection assembly 516 comprising an electrical contacting structure 518 that includes at least one cylindrical roller made of an electrically conductive material, such as any of various metals (e.g., silver, copper, aluminum), semiconductor materials, graphite, and/or conductive polymers. Specifically, the electrical contacting structure 518 may include a first cylindrical roller 520 and/or a second cylindrical roller 522. However, it should be appreciated that the electrical contacting structure 518 may include more than two cylindrical rollers in other examples. When the first cylindrical roller 520 and the second cylindrical roller 522 are included in the handle 400, the first cylindrical roller 520 and the second cylindrical roller 522 may be disposed on opposite sides of the guidewire 406 such that the guidewire 406 is sandwiched between the cylindrical rollers 520 and 522. As depicted by the arrows in FIGS. 7-9, a rotational axis 524 (shown in FIGS. 8A-9) of the cylindrical rollers 520 and 522 may be orthogonal to the central longitudinal axis 414 of the handle 400 so that when the cylindrical rollers 520 and 522 rotate, they allow the guidewire 406 to move axially relative to the handle 400.

In some examples, such as the example depicted in FIG. 7-8B, the handle 400 may include retention structures 526 that are configured to hold the cylindrical rollers 520 and 522 in place relative to the housing 402 while still permitting the cylindrical roller 520 and 522 to rotate about the rotational axis 524. For example, the retention structures 526 may comprise support rods 528 that extends through the cylindrical rollers 520 and 522. In some such examples, the cylindrical rollers 520 and 522 may each include a central aperture 530 that extends through the cylindrical rollers 520 and 522 and is configured to receive a respective support rod 528. The retention structures 526 are in turn coupled to the housing 402. In some examples, the housing 402 of the handle 400 may include notches 532 that are configured to receive and retain the ends of the rods 528. In such examples, both ends of the rods 528 may extend into the notches 532 and may be held in place via the notches 532. Thus, when the two cylindrical rollers 520, 522 are included, the housing may include four notches, one for each end of each of the rollers 520, 522. In other examples, the rods 528 may be unitary with the housing 402. For example, the rods 528 may be formed as a part of the housing 402 during the forming of the housing (e.g., during injection molding of the housing 402). Additionally or alternatively, the rods 528 may be coupled to the housing 402 via fasteners, adhesives and/or other means for coupling.

However, in other examples, such as the example depicted in FIG. 9, the handle 400 may not include the retention structures 526 and the cylindrical rollers 520 and 522 may instead be held in place by recesses 534 in the housing 402 of the handle 400. Specifically, the housing 402 may include the recesses 534, and the recesses 534 may be sized and/or shaped to receive the ends of the cylindrical rollers 520 and 522. Thus, the cylindrical rollers 520 and 522 may extend into the recesses 534 of the housing 402 and the recesses 534 may hold the cylindrical rollers 520 and 522 in place while still permitting the cylindrical rollers 520 and 522 to rotate about the rotational axis 524.

In some examples, the electrical connection assembly 516 further includes at least one electrically conductive wire 536 that is configured to electrically connect the electrical contacting structure 518 to a lead of an external electrical stimulation generator. In the illustrated example, the electrical connection assembly 516 includes wires 536 and stationary connectors 539 (shown in FIGS. 7-10) that electrically connect the rollers 520, 522 to a lead of an external electrical stimulator generator. Each electrically conductive wire 536 may comprise a first end 538 and a second end 540. The first end 538 may electrically contact one of the stationary connectors 539, and the stationary connector 539 in turn may electrically contact one of the rollers 520, 522 or one of the support rods 528.

In some examples, such as the example depicted in FIG. 8A, the stationary connectors 539 may comprise slip rings 541 that partially and/or entirely wrap around a circumference of the rollers 520, 522. In other examples, such as the examples depicted in FIGS. 8B and 10, the stationary connectors 539 may comprise electrical sockets 543 that are disposed within the recesses 534 or 634, or notches 532, of the housing 402. In examples where the electrical sockets 543 are disposed within the notches 532, the support rods 528 may comprise an electrically conductive material and thus may carry current between the electrical sockets 543 and the rollers 520, 522. In some such examples, the support rods 528 and the rollers 520, 522 may be formed as a single, unitary structure. FIG. 10 shows electrical sockets 543 spaced from electrically conductive balls 620, it should be understood that the sockets 543 can physically contact the balls 620.

The stationary connectors 539 and electrically conductive wires 536 may comprise an electrically conductive material (e.g., a metal) so that they can readily conduct electricity between the electrical contacting structures 518 and the lead of the external electrical stimulation generator.

In the examples depicted in FIGS. 7-10, both of the electrical contacting structures 518 are electrically conductive. Thus, in such examples, the handle 400 includes two wires 536 and two stationary connectors 539, wherein one of the wires 536 and one of the stationary connectors 539 electrically connect one of the electrical contacting structures 518 to the lead of the external electrical stimulation generator, and wherein the other one of the wires 536 and the other one of the stationary connectors 539 electrically connect the other electrical contacting structure 518 to the lead of the external electrical stimulation generator. However, in alternative examples, there may be only one wire 536 and one stationary connector 539 electrically connecting one of the rollers 520, 522 to the lead of an external electrical stimulator generator. In such cases, only one of the electrical contacting structures 518 (e.g., roller 520 or roller 522) need be made of an electrically conductive material. The electrical contacting structures 518 (e.g., roller(s)) not connected to a wire optionally can be made of a relatively less conductive material.

The second end 540 of each electrically conductive wire 536 may electrically connect to the lead of the external electrical stimulation generator. In some examples, the electrical connection assembly further includes an electrical socket 542 that is connected to the second ends 540 of the wires 536 and is configured to electrically contact and/or removably couple to a lead 544 of an external electrical stimulation generator 546. That is, the lead 544 of the external electrical stimulation generator 546 may be removably coupled to the electrical socket 542 to electrically connect the external electrical stimulation generator to the guidewire 406. However, in other examples, the electrical connection assembly 516 may not include an electrical socket, and instead each electrically conductive wire 536 may extend outside of the handle 400 so that it is accessible to a user. In such examples, lead 544 may be removably coupled to the external portions of the electrically conductive wires 536 (e.g., to the second ends 540 of the electrically conductive wire 536).

The external electrical stimulation generator 546 may be the same or similar to the external electrical stimulation generators 226 and 326 introduced above with reference to FIGS. 4-5. Thus, the external electrical stimulation generator 546 may similarly include a power source 548 (e.g., battery) that includes a first electrode 550 and a second electrode 552 having opposite polarities. The lead 544 is electrically connected to the second electrode 552 of the external electrical stimulation generator 546. In some examples, the second electrode 552 may be a cathode and the first electrode 550 may be an anode. Thus, in such examples, the electrical connection assembly 516 of the handle 400 may be electrically connected to the cathode of the external electrical stimulation generator 546. However, in other examples, the second electrode 552 may be an anode and the first electrode 550 may be a cathode.

In examples where an introducer device (e.g., introducer device 200 and/or 300) is used to establish an electrical connection with an external electrical stimulation generator, the introducer device and the handle 400 may be connected to electrodes of the external electrical stimulation generator having opposite polarities. For example, the handle 400 may be electrically connected to the cathode of the external electrical stimulation generator and the introducer device may be electrically connected to the anode of the external electrical stimulation generator. However, in other examples, the handle 400 may be electrically connected to the anode of the external electrical stimulation generator and the introducer device may be electrically connected to the cathode of the external electrical stimulation generator. In this way, the electrical stimulation generator may be configured to deliver electrical stimulation to a tissue of a patient via the introducer device and/or the guidewire.

In some examples, handle 400 may include at least one biasing mechanism 554 that is configured to urge the electrical contacting structure 518 toward the guidewire 406 and/or the central longitudinal axis 414 of the handle 400 to keep the electrical contacting structure 518 in electrical contact with the guidewire 406 even when the guidewire 406 and the handle 400 move relative to one another. In some examples, the biasing mechanism 554 may be a passive mechanism. For example, the biasing mechanism 554 may comprise a compression spring 556 that is biased towards an extended position in which the biasing mechanism 554 pushes the electrical contacting structure 518 into electrical contact with the guidewire 406. However, in other examples, the biasing mechanism 554 may comprise another type of passive mechanism, such as an expandable foam, or alternatively may comprise an active mechanism such as an electronically controlled actuator. When included, the compression spring 556 may comprise a first end 558 that abuts and/or is coupled to the electrical contacting structure 518 and a second end 560 that abuts and/or is coupled to an adjacent wall 562 of the housing 402. In this way, the compression spring 556 may be retained and/or otherwise held between the wall 562 of the housing 402 and the electrical contacting structure 518.

In the examples depicted in FIGS. 7-9, the handle 400 may include two compression springs 556, each of which may urge one of the rollers 520, 522 towards the guidewire 406. However, in other examples, more or less than two compression springs 556 and/or two rollers 520, 522 may be included in the handle 400.

In some examples, the biasing mechanism 554 may be configured to move (e.g., compress) to facilitate relative movement of the handle 400 and the guidewire 406. For example, the compression spring 556 may be configured to compress (move away from the extended position) to allow the guidewire 406 some degree of freedom when it moves relative to the handle 400, or vice versa.

In some examples, the electrical contacting structure 518 may include at least one stripping member 564 (as shown in FIG. 9) on an exterior surface 565 of the electrical contacting structure 518 that is configured to penetrate and/or remove an electrically insulating coating on the guidewire 406. The guidewire 406 may include such a coating (e.g., Teflon) to electrically isolate, shield, and/or otherwise protect the guidewire 406. In some such examples, the electrical contacting structure 518 may include the stripping member 564 to remove this coating so that the electrical contacting structure 518 can maintain electrical contact with the electrically conductive core of the guidewire 406.

The stripping member 564 may remove the electrically insulating coating by abrading, puncturing, cutting, and/or other fracturing the electrically insulating coating. For example, the stripping member 564 may comprise a sharp metal spike 566 that is configured to puncture the coating of the guidewire 406. In the illustrated example, as shown in FIG. 9, each roller 520, 522 comprises a stripping member in the form of a sharp metal spike 566 that is configured to contact the guidewire 406. The spikes 566 may be configured to puncture or scrape the coating of the guidewire as the rollers 520 and 522 rotate relative to the guidewire 406 when the guidewire 406 and the handle 400 move axially relative to one another. In such examples, the electrical contacting structure 518 may include a plurality of the stripping members 564 to ensure that at least one of the stripping members 564 maintains electrical contact with the electrically conductive core of the guidewire 406 as the electrical contacting structure rotates relative to the guidewire 406. As another example, the stripping member 564 may comprise an abrasive material that is configured to rub the coating off the guidewire 406. Although the stripping members are only shown in FIG. 9, it should be appreciated that the rollers 520 and 522 in the examples depicted in FIGS. 7-8B can include stripping members, such as spikes 566.

FIG. 10 depicts a cross-sectional view of the handle of FIG. 6 taken along cutting plane B-B, according to another such example. In the example of FIG. 10, handle 400 includes an electrical connection assembly 616 comprising an electrical contacting structure 618 that includes at least one spherical ball 620 made of an electrically conductive material (any of the materials disclosed above for rollers 520, 522 can be used). In some examples, the at least one spherical ball 620 may comprise two spherical balls 620, as depicted in FIG. 10, that are disposed on opposite sides of the guidewire 406. In this way, the guidewire 406 may be sandwiched between the two spherical balls 620.

However, although FIG. 10 depicts two of the spherical balls 620 it should be appreciated that more or less than two spherical balls may be included in the handle 400 in other examples. The spherical balls 620 may be retained within recesses 634 of the housing 402. Specifically, the housing 402 may include one of the recesses 634 per spherical ball 620, such that each ball 620 may be retained within its own recess. Thus, when two spherical balls 620 are included in the handle 400, the housing may include two recesses 634, each of which retains one of the two spherical balls 620.

The recesses 634 may be sized and/or shaped to receive the spherical balls 620. Specifically, the recesses 634 may be substantially spherical and may hold the spherical balls 620 in place relative to the housing 402 while permitting the spherically balls 620 to rotate relative to the housing 402 to facilitate axial movement of the guidewire 406 relative to the housing 402. In some examples, the handle 400 may include biasing mechanisms 554 (e.g., springs 556) to urge the spherical balls 620 into electrical contact with the guidewire 406. In the illustrated example, each spring 556 can be disposed in a respective recess formed in the inner surface of the housing and can have one end bearing against a respective ball 620 and another end bearing against a surface of the recess. As illustrated in FIG. 10, two springs 556 may be included in the handle 400, one for each of the two spherical balls 620. However, in other examples, the handle 400 may not include the biasing mechanisms 554 when the handle 400 includes the spherical balls 620 and/or the handle 400 may not include springs 556 for each spherical ball 620 (only some of the spherical balls 620 may have a corresponding spring 556).

Although the other optional components of the electrical connection assembly are not shown in FIG. 10 (e.g., the electrically conductive wires 536 and the electrical socket 542) it should be appreciated that the spherical balls 620 may be electrically connected to the external electrical stimulation generator in the same or similar manner as that shown and described above with reference to FIGS. 7-9. Also, as discussed above with reference to FIGS. 7-9, in some examples, each ball can be electrically connected to the generator by a respective wire; in other examples, only one of the balls may be connected to the generator by a wire.

Similarly, although the spherical balls 620 are shown without the stripping members, it should be appreciated that the spherical balls 620 may include the stripping members to remove the electrically insulating coating of the guidewire 406. Further, although the spherical balls 620 and the cylindrical rollers 520 and 522 are illustrated as two distinct examples of the electrical connection assembly, it should be appreciated that the handle 400 may include both the spherical balls 620 and the cylindrical rollers 520 and 522, in some example.

More generally, it should be appreciated that while FIGS. 7-10 depict specific examples of the handle 400, components of the handle 400 may be altered, varied, and/or used in different combinations than those shown in FIG. 7-10. For example, although cylindrical rollers and spherical balls are shown as examples of the electrical contacting structure, the electrical contacting structure may comprise alternative structures such as a toothed gear and/or a sleeve or other stationary contact that are configured to make electrical contact with the guidewire. For example, where the electrical contacting structure comprises a sleeve, the guidewire can extend through the sleeve while maintaining contact with the inner surface of the sleeve such that an electrical connection between the guidewire and the sleeve can be maintained as the guidewire and the sleeve move axially relative to each other. When the electrical contacting structure comprises a toothed gear, the teeth of the rotatable gear may be configured to penetrate the coating of the guidewire.

As another example, although the electrical contacting structure is shown as being disposed within the housing of the handle, the electrical contacting structure may be able to electrically contact the guidewire without extending into and/or inside the housing 402. As one such example, the electrical contacting structure may be positioned adjacent to and/or external to the housing, between the housing and the guidewire, but still in electrical contact with the guidewire.

Further, it should be appreciated that any of the electrical contacting structures (e.g., the spherical balls and/or the cylindrical rollers) may be included with or without the retention structures and/or the biasing mechanisms. For example, although the spherical balls 620 are illustrated without the retention structures in FIG. 10, it should be appreciated that the retention structures (e.g., rods) may be included and may extend through the spherical balls 620 to help hold them in place relative to the housing. Additionally or alternatively, it should be appreciated that different types of stationary connectors may be used to electrically contact the electrical contacting structures than those depicted in FIGS. 7-10. For example, although a slip ring is only depicted as being used in conjunction with a cylindrical roller, it should be appreciated that the slip ring may be used with other types of electrical contacting structures, such as spherical balls.

FIGS. 11-12 depict an example medical procedure in which an introducer device according to the present disclosure and/or a medical apparatus according to the present disclosure may be employed to electrically stimulate a heart.

Specifically, FIG. 11 depicts a medical assembly 700 being used to replace a native aortic valve 803 of a heart 802 of a patient 702, according to one example. Medical assembly 700 comprises an introducer device 706 and a delivery apparatus 708 (also referred to herein as "medical apparatus 708"). Introducer device 706 may be the same or similar to introducer devices 200 or 300 described above with reference to FIGS. 4-5 in that it may be configured to serve as an electrode for an electrical stimulator. Additionally or alternatively, the delivery apparatus 708 may be the same or similar to the delivery apparatus 100 described above with reference to FIGS. 2-3. Specifically, the delivery apparatus 708 comprises a handle 710 which may be the same or similar to the handle 400 described above with reference to FIGS. 6-10 in that it may be configured to electrically connect the electrical stimulator to a guidewire 712 so that the guidewire 712 can serve as an electrode. In this way, the introducer device 706 and/or the guidewire 712 may be configured to electrically stimulate the heart 802, such as to rapidly pace the heart to hold open the heart valve.

The introducer device 706 comprises a shaft 714 that is configured to be inserted into the patient 702 at an insertion site 716 (which may also be referred to herein as "surgical opening 716") and to be extended through the patient's tissue into a blood vessel 718 (e.g., femoral artery). In some examples, the introducer device 706 comprise an electrical connection assembly 720 (e.g., electrical connection assembly 204 and/or 304) that is configured to electrically connect the electrical stimulator to the patient's tissue at and/or near the insertion site 716.

The handle 710 of the medical apparatus 708 may comprise an electrical connection assembly 722 (e.g., electrical connection assembly 416, 516, and/or 616) that is configured to electrically connect the electrical stimulator to the guidewire 712. Further, the medical apparatus 708 comprises a shaft 724 that is configured to be extended through the introducer device 706 into the patient 702. For example, the shaft 724 may be configured to be advanced through the blood vessel 718 over the guidewire 712 towards and into the heart 802. A prosthetic heart valve 726 may be mounted in a crimped state on a balloon disposed along a distal end portion 728 of the shaft 724 and may be configured to be radially expanded within the native aortic valve 803 to replace the native aortic valve 803.

During the medical procedure, a user (e.g., physician or other medical personnel) may initially insert the guidewire 712 through the surgical opening 716, the blood vessel 718 and/or other vasculature of the patient 702, and the native aortic valve 803. In some examples, the user may then advance the introducer device 706 over the guidewire into the blood vessel 718 through the surgical opening 716. In some such examples, this establishes an electrical connection between the electrical connection assembly 720 of the introducer device 706 and the tissue of the patient 702. Additionally or alternatively, the user may electrically connect a first lead of the electrical stimulator to the introducer device (e.g., to an electrical socket and/or external wire of the introducer device). In this way, the introducer device may be electrically connected in series between the tissue of the blood vessel 718 (e.g., first location of the patient's vasculature) and/or the tissue at or near the surgical opening 716 and a first electrode of the electrical stimulator. However, in other examples, the user may electrically connect the first lead of the electrical stimulator to the patient's tissue at and/or near the surgical opening 716 via a needle and clip (e.g., an alligator clip), or other attachment means that is separate from the introducer device.

In addition to electrically connecting the first lead of the electrical stimulator to the patient's tissue at and/or near the insertion site 716, the user may establish an electrical connection between a second lead of the electrical stimulator and the heart 802 so that the user can electrically stimulate (e.g., rapidly pace) the heart 802. Specifically, the user may establish electrical contact between the guidewire 712 and the heart 802 (e.g., by positioning the guidewire 712 in electrical contact with tissue of the heart 802) and may electrically connect a second lead of the electrical stimulator to the electrical connection assembly 722 (e.g., external wire or electrical socket of the electrical connection assembly 722) of the handle 710 of the medical apparatus 708. Further, the user may electrically connect the electrical connection assembly 722 to the guidewire 712 by advancing the delivery apparatus 708 over the guidewire 712, since the electrical connection assembly 722 is configured to electrically contact the guidewire 712 when the guidewire 712 is received within the handle 710. In this way, the handle 710 (and specifically the electrical connection assembly 722 of the handle 710) may be electrically connected in series between the guidewire 712 and the second lead and second electrode of the electrical stimulator.

The user advances the medical apparatus 708 over the guidewire 712 into and through the vasculature of the patient 702 until the shaft 724 of the medical apparatus 708 reaches the heart 802. In particular, the user may advance the distal end portion 728 of the shaft 724 until the prosthetic heart valve 726 nears and/or reaches the native aortic valve 803. For example, the delivery apparatus 708 can be advanced until the prosthetic valve 726 is located within the aortic root, as shown in FIG. 11. At this point, the user may electrically stimulate the heart 802 (e.g., rapidly pace the heart) to hold the native leaflets of the native aortic valve 803 open while positioning, expanding and/or otherwise deploying the prosthetic heart valve 726 within the native aortic valve 803.

Because the electrical connection assembly 722 of the handle 710 is configured to maintain an electrical connection between the guidewire 712 and the electrical stimulator once the handle 710 has been advanced over the guidewire 712, the guidewire 712 and/or the medical apparatus 708 may be repositioned as desired during the medical procedure without disconnecting the guidewire 712 from the electrical stimulator, thus allowing the user to more simply and easily electrically stimulate the heart 802.

FIG. 12 depicts an enlarged view of the distal end portion 728 of the shaft 724 of the medical apparatus 708 being inserted into the heart 802 to replace the native aortic valve 803 (such as during a TAVI procedure), according to one example. As shown in FIG. 12, the guidewire 712 may be advanced through the aorta 804, the native aortic valve 803, and into a left ventricle 806. Further, the guidewire 712 may electrically contact the tissue of the left ventricle 806, as illustrated in FIG. 12, so that the guidewire 712 can serve as an electrode for an electrical stimulator. The shaft 724 may be advanced over the guidewire 712 until the prosthetic heart valve 726 is adjacent the native aortic valve 803 within the aortic root or ascending aorta, as illustrated in FIG. 12. A user may then electrically stimulate the heart 802 to hold open the native leaflets 808 of the native aortic valve 803. While the heart is stimulated, the user further advances the delivery apparatus to position the prosthetic valve 726 between the native leaflets 808, deploys the prosthetic valve by inflating the balloon of the delivery apparatus to expand the prosthetic valve into engagement with the tissue of the native valve, then deflates the balloon. Following deflation of the balloon, pacing of the heart can be discontinued and the delivery apparatus can be removed from the body.

Although FIGS. 11-12 depict the handle of the medical apparatus being used during an aortic valve replacement procedure (e.g., TAVI procedure), it should be appreciated that the handle may be used during the replacement of other heart valves such as the mitral, tricuspid, and/or pulmonary valves to provide an electrical connection between the guidewire and the electrical stimulator. Further, although FIGS. 11-12 depict the handle of the medical apparatus being used during a heart valve replacement procedure (to provide an electrical connection between the guidewire and the electrical stimulator), it should be appreciated that the medical apparatus may be used during other types of medical procedures to electrically stimulate the heart. For example, the handle of the medical apparatus may be employed during valvuloplasty to electrically connect the guidewire and the electrical stimulator to electrically stimulate the heart. Further, the handle of the medical apparatus may be used to electrically connect the guidewire to the electrical stimulator to stimulate other organs, tissue, and/or regions of the body besides the heart by positioning the guidewire in electrical contact with these other organs, tissue and/or region of the body. So long as the guidewire is in electrical contact with some bodily fluid and/or organ, the guidewire can serve as an electrode and provide electrical stimulation to the bodily fluid and/or organ when a handle according to the present disclosure is advanced over the guidewire.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A medical apparatus for insertion into a patient's vasculature via catheterization, comprising:

a handle comprising:
- a housing configured to be slidably coupled to a guidewire when the guidewire is inserted through the housing; and
- an electrical connection assembly that is configured to be electrically connected to an electrode of an external electrical stimulation generator and to the guidewire to provide an electrical connection between the external electrical stimulation generator and the guidewire, the electrical connection assembly comprising:
- at least one electrical contacting structure configured to maintain electrical contact with the guidewire as the guidewire moves longitudinally relative to the handle, or vice versa.

Example 2. The medical apparatus of any example herein, particularly example 1, wherein the electrical connection assembly further comprises a stationary connector that electrically contacts the electrical contacting structure, and an electrical connector that is electrically connected to the stationary connector and that is configured to be removably coupled and electrically connected to a lead of the external electrical stimulation generator.

Example 3. The medical apparatus of any example herein, particularly example 2, wherein the electrical connector comprises an electrical socket on an exterior of the housing that is configured to be removably coupled and electrically connected to the lead of the external electrical stimulation generator, and wherein the electrical connector further comprises an electrically conductive wire, wherein a first end of the electrically conductive wire electrically connects to the stationary connector and wherein an opposite second end of the electrically conductive wire electrically connects to the electrical socket to provide an electrical connection between the electrical socket and the electrical contacting structure.

Example 4. The medical apparatus of any example herein, particularly example 2, wherein the electrical connector comprises an electrically conductive wire, wherein a first end of the electrically conductive wire electrically connects to the stationary connector and wherein an opposite second end of the electrically conductive wire extends outside of the housing through a socket in the housing, and wherein the second end of the electrically conductive wire is configured to be removably coupled and electrically connected to the lead of the external electrical stimulation generator.

Example 5. The medical apparatus of any example herein, particularly any of examples 1-4, wherein the housing has an internal passageway that extends through the housing and is configured to receive the guidewire.

Example 6. The medical apparatus of any example herein, particularly example 5, wherein the housing comprises a recess along the internal passageway, and wherein the electrical contacting structure is disposed within the recess.

Example 7. The medical apparatus of any example herein, particularly any of examples 1-6, further comprising a biasing mechanism that urges the electrical contacting structure toward the guidewire.

Example 8. The medical apparatus of any example herein, particularly example 7, wherein the biasing mechanism comprises a compression spring.

Example 9. The medical apparatus of any example herein, particularly example 8, wherein a first end of the compression spring abuts an adjacent surface of the housing, and wherein an opposite second end of the compression spring abuts the electrical contacting structure.

Example 10. The medical apparatus of any example herein, particularly any of examples 1-9, wherein the electrical contacting structure comprises at least one cylindrical roller.

Example 11. The medical apparatus of any example herein, particularly example 10, further comprising a retention structure that is configured to hold the cylindrical roller in place relative to the housing.

Example 12. The medical apparatus of any example herein, particularly example 11, wherein the retention structure comprises a support rod that extends through the electrical contacting structure and that is coupled on either end to the housing.

Example 13. The medical apparatus of any example herein, particularly example 12, wherein the housing further comprises notches that receive and retain the cylindrical roller.

Example 14. The medical apparatus of any example herein, particularly example 12 or 13, wherein the cylindrical roller comprises a central aperture through which the support rod extends.

Example 15. The medical apparatus of any example herein, particularly any of examples 10-14, wherein the at least one cylindrical roller comprises a first cylindrical roller and a second cylindrical roller that are disposed on opposite sides of the guidewire.

Example 16. The medical apparatus of any example herein, particularly any of examples 1-9, wherein the electrical contacting structure comprises at least one spherical ball.

Example 17. The medical apparatus of any example herein, particularly example 16, wherein the at least one spherical ball comprises a plurality of spherical balls.

Example 18. The medical apparatus of any example herein, particularly any of examples 1-17, wherein the electrical contacting structure comprises at least one stripping member that protrude from an external surface of the electrical contacting structure and that are configured to penetrate a coating of the guidewire.

Example 19. The medical apparatus of any example herein, particularly example 18, wherein the at least one stripping member comprises at least one metal spike.

Example 20. The medical apparatus of any example herein, particularly any of examples 1-19, wherein a rotational axis of the electrical contacting structure is orthogonal to a/the central axis of a/the internal passageway of the housing that is configured to receive the guidewire.

Example 21. The medical apparatus of any example herein, particularly any of examples 1-20, further comprising a locking mechanism that is configured to be selectively adjusted by a user to prevent axial movement of the guidewire relative to the handle.

Example 22. The medical apparatus of any example herein, particularly any of examples 1-21, further comprising a shaft that extends distally from the handle, and that is configured to be inserted into the patient's vasculature.

Example 23. The medical apparatus of any example herein, particularly example 22, further comprising an inflatable balloon positioned on a distal end portion of the shaft.

Example 24. The medical apparatus of any example herein, particularly any of examples 22-23, wherein the shaft comprises a steerable shaft that is configured to be navigated through the patient's vasculature.

Example 25. A medical assembly for rapidly pacing a heart of a patient, the medical assembly comprising:

an introducer device that is configured to be electrically connected to a first location within a vasculature of the patient and to be electrically connected to a first electrode of an electric power source, the first electrode having a first polarity; and a medical apparatus that is configured to be inserted through the introducer device, wherein the medical apparatus is configured to be electrically connected to a second electrode of the electric power source and is configured to be electrically connected to a guidewire that is electrically connected to a second location within the vasculature of the patient, and wherein the second electrode has a second polarity that is opposite the first polarity of the first electrode.

Example 26. The medical assembly of any example herein, particularly example 25, further comprising the electric power source, wherein the electric power source comprises the first electrode and the second electrode.

Example 27. The medical assembly of any example herein, particularly any of examples 25 or 26, further comprising the guidewire, wherein the guidewire is configured to extend into the vasculature of the patient and through a native valve of the heart, and wherein the introducer device and the medical apparatus are configured to be advanced over the guidewire.

Example 28. The medical assembly of any example herein, particularly any of examples 25-27, wherein the introducer device is configured to be electrically connected in series between the first location of the vasculature and the first electrode of the electric power source.

Example 29. The medical assembly of any example herein, particularly any of examples 25-28, wherein the medical apparatus is configured to be electrically connected in series between the guidewire and the second electrode of the electric power source.

Example 30. The medical assembly of any example herein, particularly any of examples 25-29, wherein the introducer device comprises a lumen that is configured to receive the medical apparatus and the guidewire.

Example 31. The medical assembly of any example herein, particularly example 30, wherein the medical apparatus is configured to be extended through the lumen of the introducer device.

Example 32. The medical assembly of any example herein, particularly any of examples 25-31, wherein the introducer device further comprises an electrical connection assembly that is configured to be electrically connected to the first location of the vasculature, and that is configured to be removably coupled and electrically connected to a first lead of the electric power source to provide an electrical connection between the first electrode of the electric power source and the first location of the vasculature.

Example 33. The medical assembly of any example herein, particularly example 32, wherein the electrical connection assembly comprises an electrically conductive wire that extends inside the introducer device.

Example 34. The medical assembly of any example herein, particularly example 33, wherein the electrical connection assembly further comprises an electrical socket that electrically connects to the electrically conductive wire, and that is configured to be removably coupled and electrically connected to the first lead of the electric power source.

Example 35. The medical assembly of any example herein, particularly example 33, wherein a proximal end of the electrically conductive wire extends outside of the introducer device through a fluid port of the introducer device, and wherein the proximal end of the electrically conductive wire is configured to be removably coupled and electrically connected to the first lead of the electric power source.

Example 36. The medical assembly of any example herein, particularly any of examples 33-35, wherein the introducer device comprises an electrically conductive contacting element on an exterior surface of the introducer device that is configured to be electrically connected to the first location of the vasculature.

Example 37. The medical assembly of any example herein, particularly example 36, wherein the electrically conductive contacting element comprises an exposed portion of the electrically conductive wire, and wherein the introducer device comprises an aperture through which the exposed portion of the electrically conductive wire protrudes.

Example 38. The medical assembly of any example herein, particularly example 36, wherein the electrically conductive contacting element comprises a metal braid, and wherein the electrically conductive wire electrically connects to the electrically conductive contacting element.

Example 39. The medical assembly of any example herein, particularly any of examples 25-38, wherein the medical apparatus comprises a handle comprising:

a housing slidably coupled to the guidewire; and an electrical connection assembly that is configured to be electrically connected to the second electrode of the electric power source and to the guidewire to provide an electrical connection between the second electrode of the electric power source and the guidewire, the electrical connection assembly comprising:

at least one electrical contacting structure configured to maintain electrical contact with the guidewire as the guidewire moves longitudinally relative to the handle, or vice versa.

Example 40. The medical assembly of any example herein, particularly example 39, wherein the medical apparatus further comprises a shaft that extends distally from the handle, and that is configured to be inserted into the vasculature of the patient.

Example 41. The medical assembly of any example herein, particularly example 40, further comprising a prosthetic heart valve that is removably coupled to a distal end portion of the shaft.

Example 42. The medical assembly of any example herein, particularly any of examples 40-41, wherein the medical apparatus further comprises an inflatable balloon positioned at a/the distal end of the shaft, wherein the inflatable balloon is configured to expand and deploy a/the prosthetic heart valve.

Example 43. The medical assembly of any example herein, particularly any of examples 40-42, wherein the shaft comprises a steerable shaft that is configured to be navigated through the vasculature of the patient.

Example 44. The medical assembly of any example herein, particularly any of examples 39-43, wherein the electrical connection assembly of the handle of the medical apparatus further comprises a stationary connector that electrically contacts the electrical contacting structure, and an electrical connector that is electrically connected to the stationary connector and that is configured to be removably coupled and electrically connected to a second lead of the electric power source.

Example 45. The medical assembly of any example herein, particularly example 44, wherein the electrical connector comprises an electrical socket on an exterior of the housing that is configured to be removably coupled and electrically connected to the second lead of the electric power source, and wherein the electrical connector further comprises an electrically conductive wire, wherein a first end of the electrically conductive wire electrically connects to the stationary connector and wherein an opposite second end of the electrically conductive wire electrically connects to the electrical socket to provide an electrical connection between the electrical socket and the electrical contacting structure.

Example 46. The medical assembly of any example herein, particularly example 44, wherein the electrical connector comprises an electrically conductive wire, wherein a first end of the electrically conductive wire electrically connects to the stationary connector and wherein an opposite second end of the electrically conductive wire extends outside of the housing, and wherein the second end of the electrically conductive wire is configured to be removably coupled and electrically connected to the second lead of the electric power source.

Example 47. The medical assembly of any example herein, particularly any of examples 39-46, wherein the housing has an internal passageway that extends through the housing and is configured to receive the guidewire.

Example 48. The medical assembly of any example herein, particularly example 47, wherein the housing comprises a recess along the internal passageway, and wherein the electrical contacting structure is disposed within the recess.

Example 49. The medical assembly of any example herein, particularly any of examples 39-48, wherein the handle further comprises a biasing mechanism that urges the electrical contacting structure toward the guidewire and/or a central axis of a/the internal passageway.

Example 50. The medical assembly of any example herein, particularly example 49, wherein the biasing mechanism comprises a compression spring.

Example 51. The medical assembly of any example herein, particularly example 50, wherein a first end of the compression spring abuts an adjacent surface of the housing, and wherein an opposite second end of the compression spring abuts the electrical contacting structure.

Example 52. The medical assembly of any example herein, particularly any of examples 39-51, wherein the electrical contacting structure comprises at least one cylindrical roller.

Example 53. The medical assembly of any example herein, particularly example 52, wherein the handle further comprises a retention structure that is configured to hold the cylindrical roller in place relative to the housing.

Example 54. The medical assembly of any example herein, particularly example 53, wherein the retention structure comprises a support rod that extends through the electrical contacting structure and that is coupled on either end to the housing.

Example 55. The medical assembly of any example herein, particularly example 54, wherein the housing further comprises notches that receive and retain the cylindrical roller.

Example 56. The medical assembly of any example herein, particularly example 54 or 55, wherein the cylindrical roller comprises a central aperture through which the support rod extends.

Example 57. The medical assembly of any example herein, particularly any of examples 52-56, wherein the at least one cylindrical roller comprises a first cylindrical roller and a second cylindrical roller that are disposed on opposite sides of the guidewire.

Example 58. The medical assembly of any example herein, particularly any of examples 39-57, wherein the electrical contacting structure comprises at least one spherical ball.

Example 59. The medical assembly of any example herein, particularly example 58, wherein the at least one spherical ball comprises a plurality of spherical balls.

Example 60. The medical assembly of any example herein, particularly any of examples 39-59, wherein the electrical contacting structure comprises at least one stripping member that protrude from an external surface of the electrical contacting structure and that are configured to penetrate a coating of the guidewire.

Example 61. The medical assembly of any example herein, particularly example 60, wherein the at least one stripping member comprises at least one metal spike.

Example 62. The medical assembly of any example herein, particularly any of examples 39-61, wherein a rotational axis of the electrical contacting structure is orthogonal to a/the central axis of a/the internal passageway of the housing that is configured to receive the guidewire.

Example 63. The medical assembly of any example herein, particularly any of examples 39-62, wherein the handle further comprises a locking mechanism that is configured to be selectively adjusted by a user to prevent axial movement of the guidewire relative to the handle.

Example 64. A medical assembly for rapidly pacing a heart, the medical assembly comprising:

an electric power source comprising a first electrode having a first polarity and a second electrode having a second polarity that is opposite the first polarity;

a guidewire that is configured to be inserted into a vasculature of a patient and through a native valve of a heart of the patient, wherein the guidewire is configured to be electrically connected to the vasculature at a first location of the vasculature;

an introducer device configured to extend over the guidewire, wherein the introducer device is configured to be electrically connected to the vasculature at a second location of the vasculature, and wherein the introducer device is configured to be electrically connected to the second electrode of the electric power source to provide an electrical connection between the second electrode of the electric power source and the second location of the vasculature; and a medical apparatus configured to extend over the guidewire and through the introducer device, wherein the medical apparatus is configured to be electrically connected to the first electrode of the electric power source and is further configured to be electrically connected to the guidewire to provide an electrical connection between the first electrode of the electric power source and the first location of the vasculature.

Example 65. The medical assembly of any example herein, particularly example 64, wherein the medical apparatus is the medical apparatus of any of examples 1-24.

Example 66. A method for rapidly pacing a heart with a medical apparatus, the method comprising:

inserting a guidewire through a surgical opening, a vasculature of a patient, and a native valve of a heart of the patient;

advancing the medical apparatus over the guidewire into and through the vasculature;

establishing an electrical connection between a first lead of an external power source and tissue of the patient to electrically connect the tissue with the external power source;

electrically connecting a second lead of the external power source to an electrical connection assembly included within a handle of the medical apparatus;

establishing electrical contact between the guidewire and cardiac tissue;

establishing electrical contact between the guidewire and the electrical connection assembly of the medical apparatus to electrically connect the cardiac tissue with the external power source; and electrically stimulating the heart with the external power source.

Example 67. The method of any example herein, particularly example 66, further comprising inserting an introducer device into the vasculature before advancing the medical apparatus, and wherein the advancing the medical apparatus further comprises advancing the medical apparatus through the introducer device.

Example 68. The method of any example herein, particularly example 67, wherein the establishing the electrical connection between the first lead of the external power source and the tissue of the patient comprises establishing electrical contact between an electrical connection assembly of the introducer device and tissue of the vasculature.

Example 69. The method of any example herein, particularly example 67 or 68, wherein the establishing the electrical connection between the first lead of the external power source and the tissue of the patient comprises removably coupling the first lead to an electrical socket of the introducer device.

Example 70. The method of any example herein, particularly example 67 or 68, wherein the establishing the electrical connection between the first lead of the external power source and the tissue of the patient comprises removably coupling the first lead to an electrically conductive wire that extends into and through the introducer device.

Example 71. The method of any example herein, particularly example 66 or 67, wherein the establishing the electrical connection between the first lead of the external power source and the tissue of the patient comprises establishing electrical contact between the first lead of the external power source and tissue of the patient that is adjacent to the surgical opening.

Example 72. The method of any example herein, particularly any of examples 66-71, wherein the establishing electrical contact between the guidewire and the electrical connection assembly comprises establishing electrical contact between the guidewire and an electrical contacting structure of the electrical connection assembly.

Example 73. The method of any example herein, particularly example 72, wherein the electrical contacting structure is disposed within and/or located at a passageway of the handle of the medical apparatus.

Example 74. The method of any example herein, particularly any of examples 66-73, wherein electrically connecting a second lead of the external power source to an electrical connection assembly included within a handle of the medical apparatus comprises removably coupling the second lead to an electrical socket of the electrical connection assembly included on an exterior of the handle.

Example 75. The method of any example herein, particularly any of examples 66-73, wherein electrically connecting a second lead of the external power source to an electrical connection assembly included within a handle of the medical apparatus comprises removably coupling the second lead to an electrically conductive wire of the electrical connection assembly that extends inside the handle.

In view of the many possible examples to which the principles of the disclosed invention may be applied, it should be recognized that the illustrated examples are only preferred examples of the invention and should not be taken as limiting the scope of the invention. Rather, the scope of the invention is defined by the following claims. We therefore claim as our invention all that comes within the scope and spirit of these claims.

The invention claimed is:

1. A medical apparatus for insertion into a patient's vasculature via catheterization, comprising:

a handle comprising:

a housing configured to be slidably coupled to a guidewire inserted into the patient's vasculature such that the housing can be advanced over the guidewire with the guidewire extending completely through the housing and a proximal portion of the guidewire extending proximally beyond a proximal end of the handle; and an electrical connection assembly that is configured to be electrically connected to an electrode of an external electrical stimulation generator and to the guidewire to provide an electrical connection between the external electrical stimulation generator and the guidewire, the electrical connection assembly comprising:

at least one electrical contacting structure configured to maintain electrical contact with the guidewire and the external electrical stimulation generator as the guidewire moves longitudinally relative to the handle, or vice versa.

2. The medical apparatus of claim 1, wherein the electrical connection assembly further comprises a stationary connector that electrically contacts the electrical contacting structure, and an electrical connector that is electrically connected to the stationary connector and that is configured to be removably coupled and electrically connected to a lead of the external electrical stimulation generator.

3. The medical apparatus of claim 2, wherein the electrical connector comprises an electrical socket on an exterior of the housing that is configured to be removably coupled and electrically connected to the lead of the external electrical stimulation generator, and wherein the electrical connector further comprises an electrically conductive wire, wherein a first end of the electrically conductive wire electrically connects to the stationary connector and wherein an opposite second end of the electrically conductive wire electrically connects to the electrical socket to provide an electrical connection between the electrical socket and the electrical contacting structure.

4. The medical apparatus of claim 2, wherein the electrical connector comprises an electrically conductive wire, wherein a first end of the electrically conductive wire electrically connects to the stationary connector and wherein an opposite second end of the electrically conductive wire extends outside of the housing through a socket in the housing, and wherein the second end of the electrically conductive wire is configured to be removably coupled and electrically connected to the lead of the external electrical stimulation generator.

5. The medical apparatus of claim 1, wherein the housing has an internal passageway that extends through the housing and is configured to receive the guidewire.

6. The medical apparatus of claim 5, wherein the housing comprises a recess along the internal passageway, and wherein the electrical contacting structure is disposed within the recess.

7. The medical apparatus of claim 1, further comprising a biasing mechanism that urges the electrical contacting structure toward the guidewire.

8. The medical apparatus of claim 7, wherein the biasing mechanism comprises a compression spring.

9. The medical apparatus of claim 8, wherein a first end of the compression spring abuts an adjacent surface of the housing, and wherein an opposite second end of the compression spring abuts the electrical contacting structure.

10. The medical apparatus of claim 1, wherein the electrical contacting structure comprises at least one cylindrical roller.

11. The medical apparatus of claim 10, further comprising a retention structure that is configured to hold the cylindrical roller in place relative to the housing.

12. The medical apparatus of claim 11, wherein the retention structure comprises a support rod that extends through the electrical contacting structure and that is coupled on either end to the housing.

13. The medical apparatus of claim 12, wherein the housing further comprises notches that receive and retain the cylindrical roller.

14. The medical apparatus of claim 12, wherein the cylindrical roller comprises a central aperture through which the support rod extends.

15. The medical apparatus of claim 10, wherein the at least one cylindrical roller comprises a first cylindrical roller and a second cylindrical roller that are disposed on opposite sides of the guidewire.

16. The medical apparatus of claim 1, wherein the electrical contacting structure comprises at least one spherical ball.

17. The medical apparatus of claim 16, wherein the at least one spherical ball comprises a plurality of spherical balls.

18. The medical apparatus of claim 1, wherein the electrical contacting structure comprises at least one stripping member that protrude from an external surface of the electrical contacting structure and that are configured to penetrate a coating of the guidewire.

19. The medical apparatus of claim 18, wherein the at least one stripping member comprises at least one metal spike.

20. The medical apparatus of claim 1, wherein a rotational axis of the electrical contacting structure is orthogonal to a central axis of an internal passageway of the housing that is configured to receive the guidewire.

21. The medical apparatus of claim 1, further comprising a locking mechanism that is configured to be selectively adjusted by a user to prevent axial movement of the guidewire relative to the handle.

22. The medical apparatus of claim 1, further comprising a shaft that is connected to and extends distally from the handle, and that is configured to be inserted into the patient's vasculature.

23. The medical apparatus of claim 22, further comprising an inflatable balloon positioned on a distal end portion of the shaft.

* * * * *